(12) United States Patent
Kawagishi et al.

(10) Patent No.: US 8,454,514 B2
(45) Date of Patent: Jun. 4, 2013

(54) ULTRASOUND DIAGNOSTIC APPARATUS AND A MEDICAL IMAGE-PROCESSING APPARATUS

(75) Inventors: Tetsuya Kawagishi, Nasushiobara (JP); Yasuhiko Abe, Otawara (JP); Shinichi Hashimoto, Otawara (JP); Muneki Kataguchi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1346 days.

(21) Appl. No.: 11/862,590

(22) Filed: Sep. 27, 2007

(65) Prior Publication Data

US 2008/0077013 A1    Mar. 27, 2008

(30) Foreign Application Priority Data

Sep. 27, 2006  (JP) .................................. 2006-262864

(51) Int. Cl.
    *A61B 8/00*        (2006.01)
(52) U.S. Cl.
    USPC ............ 600/443; 600/407; 600/437; 382/128
(58) Field of Classification Search
    USPC .................................. 600/437, 443; 382/128
    See application file for complete search history.

(56) References Cited

U.S. PATENT DOCUMENTS

| 2004/0081340 | A1* | 4/2004 | Hashimoto | 382/128 |
| 2005/0251037 | A1 | 11/2005 | Watanabe et al. | |
| 2010/0185094 | A1* | 7/2010 | Hamada et al. | 600/443 |
| 2010/0268085 | A1* | 10/2010 | Kruecker et al. | 600/443 |
| 2010/0309198 | A1* | 12/2010 | Kauffmann | 345/419 |
| 2011/0077516 | A1* | 3/2011 | Abe | 600/443 |

FOREIGN PATENT DOCUMENTS

| JP | 04-176447 | 6/1992 |
| JP | 2002-177265 | 6/2002 |
| JP | 2005-304757 | 11/2005 |
| JP | 2006-006671 | 1/2006 |
| JP | 2006-212164 | 8/2006 |
| JP | 2006-312026 | 11/2006 |
| WO | WO 2006/059668 | 6/2006 |

OTHER PUBLICATIONS

U.S. Appl. No. 12/793,112, filed Jun. 3, 2010, Hashimoto, et al.
Japanese Office Action issued Jul. 31, 2012, in Japanese Patent Application No. 2006-262864 filed Sep. 27, 2006.

* cited by examiner

*Primary Examiner* — Unsu Jung
*Assistant Examiner* — Amanda Lauritzen
(74) *Attorney, Agent, or Firm* — Oblon, Spivak, McClelland, Maier & Neustadt, L.L.P.

(57) ABSTRACT

An ultrasound diagnostic apparatus 1 comprises an ultrasonic probe 2 for transmitting the ultrasound while three-dimensionally scanning, and receiving ultrasound reflected from biological tissue, an image processor 5 (and a signal processor 4) for generating image data for an MPR image based on results received thereof, an information memory 6 for storing cross-sectional-position information D showing a cross-section of this MPR image, a display part 81, and a controller 9. The image processor 5 generates image data for the new MPR image for the relevant cross-sectional position, based on the cross-sectional position shown in the cross-sectional-position information D1 obtained when the MPR image was obtained in the past and the received results obtained by the new three-dimensional scan performed with the ultrasonic probe 2. The controller 9 causes the display part 81 to display the new MPR image.

6 Claims, 16 Drawing Sheets

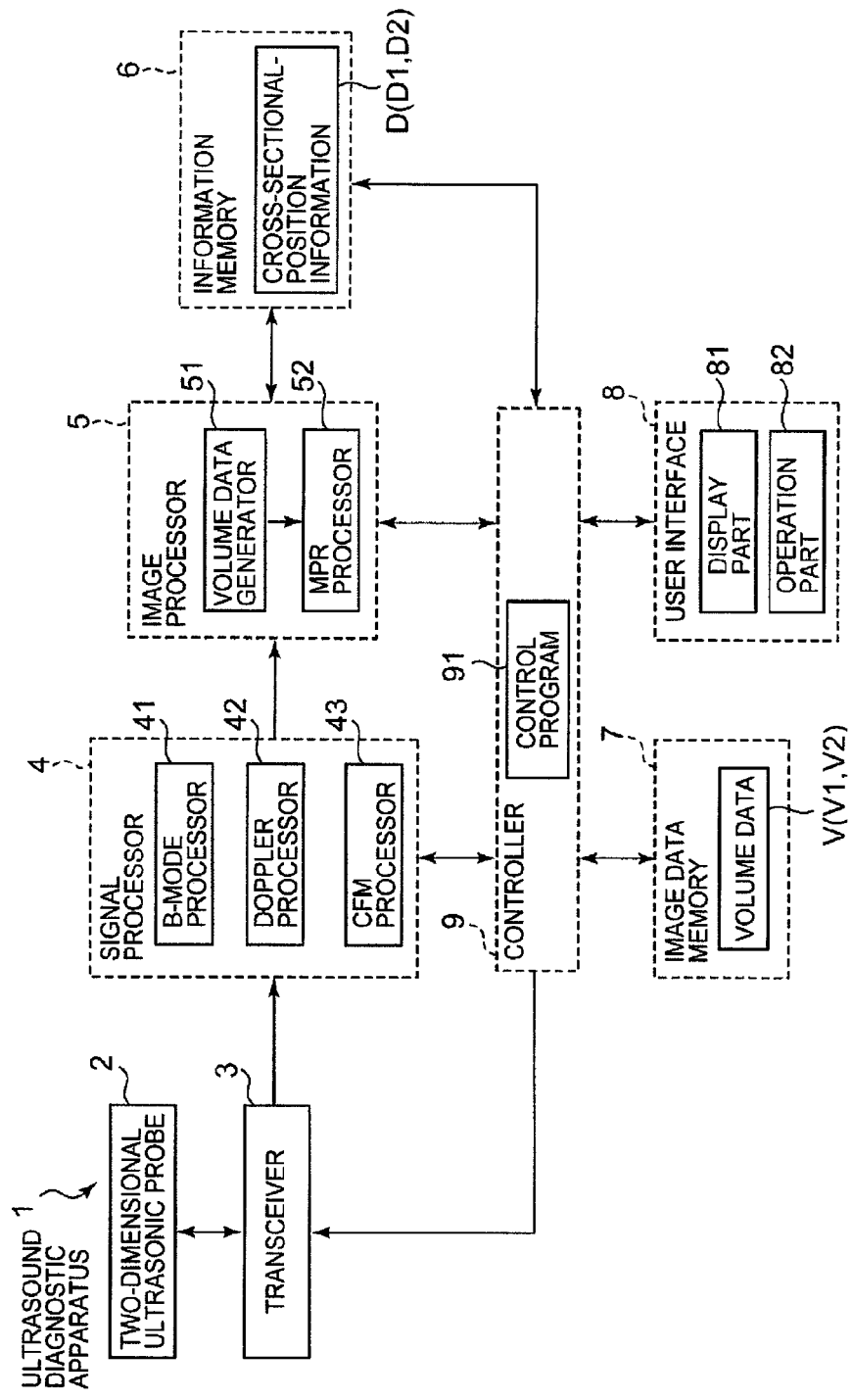

US 8,454,514 B2

ULTRASOUND DIAGNOSTIC APPARATUS AND A MEDICAL IMAGE-PROCESSING APPARATUS

CROSS-REFERENCE TO RELATED APPLICATIONS

This application claims priority to foreign application JP 2006-262864, filed Sep. 27, 2006, which is incorporated herein by reference.

BACKGROUND OF THE INVENTION

1. Field of the Invention

The present invention relates to an ultrasound diagnostic apparatus and a medical image-processing apparatus. The ultrasound diagnostic apparatus is an apparatus that transmits ultrasound to the inside of a subject using an ultrasonic probe, and obtains medical images of the subject based on waves reflected therefrom. The medical image-processing apparatus is an apparatus for processing medical images obtained by the ultrasound diagnostic apparatus. In particular, the present invention relates to the art used for comparative evaluation of motor functions of the same biological tissue obtained at different timing.

2. Description of the Related Art

The ultrasound diagnostic apparatus has a merit whereby it is possible to observe an image instantly by a simple operation such as the operation of simply placing the ultrasonic probe in contact with a body surface. Thus, the ultrasound diagnostic apparatus has been widely used to diagnose the shape and function of biological tissue. In recent years, more attention is being paid to an evaluation of a motor function of biological tissue, such as heart wall motion, and especially an evaluation of a three-dimensional motor function.

Additionally, the ultrasound diagnostic apparatus is used for obtaining images of biological tissue at a plurality of times at different timing (time and days), comparing such images, and thereby observing the time elapsed changes in condition of the biological tissue. A typical example of such a use includes stress echocardiography. Other than that, the ultrasound diagnostic apparatus is used in observation of a clinical course, preoperative/postoperative observation, and so on.

Stress echocardiography is an examination for evaluating the motor function of a heart by comparing an image obtained at a time when a patient is not subjected to stress such as motion or medication, with an image obtained at a time in which the patient is subjected to stress. There is also an examination for evaluating heart function by applying stress in stages and comparing images of the respective phases (e.g., refer to Japanese Unexamined Patent Application Publication No. 2005-304757).

In stress echocardiography using two-dimensional images, images are obtained from multiple views (tomographic planes) for each phase of the stress. Examples of such images include views such as an apical four-chamber view, an apical two-chamber view, a long-axis view of the left ventricle, and a short-axis view of the left ventricle.

Additionally, in recent years, stress echocardiography using three-dimensional images has been proposed. This method is to generate, at each phase of the stress, volume data by three-dimensionally scanning ultrasound, and obtain a desired cross-sectional image by subjecting this volume data to MPR (Multi-Planar Reconstruction).

However, regarding a conventional ultrasound diagnostic apparatus the following problems are pointed out. Firstly, there has been a problem in which stress echocardiography using two-dimensional images needs to variously change the way in which the ultrasonic probe is placed on the subject in order to obtain multiple images as described above, resulting in a complicated and long-time examination.

Secondly, although an image of the short-axis viewal view of the left ventricle is suitable for the observation of heart wall motion, it is possible in stress echocardiography using two-dimensional images, to obtain only short-axis tomographic images at the papillary muscle level, so that there has been a problem in which the condition of the left ventricle cannot be observed comprehensively.

Meanwhile, stress echocardiography using three-dimensional images is to obtain volume data at each phase to generate an MPR image and thus designate a cross-section that makes it possible to adequately observe the condition of the cardiac muscle. However, there has been a problem in which this operation is highly complicated and time consuming.

Additionally, because there has been no means for comparative observation by displaying both a past MPR image and a new MPR image, it has been particularly troublesome and time consuming to match a cross-sectional position of a past MPR image with a cross-sectional position of a new MPR image.

Furthermore, in the comparative observation, it is preferable to observe tomographic images at the same cross-section for each phase, but it has been difficult to set the same cross-section for each phase in a conventional configuration.

Moreover, even in the case of three-dimensionally scanning ultrasound, it is still necessary to place the ultrasonic probe properly on the subject in order to observe the condition of biological tissue. However, it is not possible to verify the manner of placement of the ultrasonic probe until an image is displayed for viewing.

Therefore, it has been particularly troublesome and time consuming to determine the manner of placement of an ultrasonic probe.

In addition, even in the case of observation of the clinical course, preoperative/postoperative observation, and the like, it has been difficult to designate the same cross-section for each timing when tomographic images based on volume data obtained at different timings are comparatively observed.

SUMMARY OF THE INVENTION

The present invention was made in order to solve the aforementioned problems, and an object of the present invention is to provide an ultrasound diagnostic apparatus and a medical image-processing apparatus that are capable of easily obtaining tomographic images of the same cross section of biological tissue in an examination for observing time-elapsed changes of the biological tissue.

Further, another object of the present invention is to provide an ultrasound diagnostic apparatus and a medical image-processing apparatus that are capable of making an examination for observing time-elapsed changes of biological tissue simple and short-time.

In a first aspect of the present invention, an ultrasound diagnostic apparatus comprises: an ultrasonic probe configured to transmit ultrasound while three-dimensionally scanning, and receive ultrasound reflected by a biological tissue; an image data generator configured to generate image data of a tomographic image of the biological tissue based on reception results of ultrasound; a memory configured to store cross-sectional-position information showing a cross-section a position of the tomographic image; a display part; and a controller configured to: control the image data generator so as to, based on a cross-sectional position shown in crosssectional-position information obtained when image data of a tomographic image of the biological tissue has been generated previously, and reception results of new ultrasound, generate image data of a new tomographic image in the relevant cross-sectional position; and cause the display part to display the new tomographic image.

According to the first aspect, it is possible to, based on a cross-sectional position shown in past cross-sectional-position information and reception results of new ultrasound, generate and display a new tomographic image in a past cross-sectional position. Consequently, it is possible to easily obtain a tomographic image of the same cross section of a biological tissue, in an examination of observing time change of the biological tissue.

In a second aspect of the present invention, an ultrasound diagnostic apparatus comprises: an ultrasonic probe configured to transmit ultrasound while scanning, and receive ultrasound reflected by a biological tissue; an image data generator configured to generate image data of a tomographic image of the biological tissue, based on reception results of ultrasound; a memory configured to store scanning position information showing a scanning position of ultrasound by the ultrasonic probe; a display part; and a controller configured to: control the ultrasonic probe at the time of generation of image data of a new tomographic image of the biological tissue so as to transmit ultrasound to a scanning position shown in scanning position information obtained at the time of past generation of image data of a tomographic image; control the image data generator so as to generate image data of a new tomographic image based on reception results of the ultrasound; and cause the display part to display the new tomographic image.

According to the second aspect, it is possible to transmit ultrasound to a scanning position shown in past scanning position information, and generate and display a new tomographic image based on reception results of this ultrasound. Consequently, it is possible to easily obtain a tomographic image of the same cross section of a biological tissue, in an examination of observing time change of the biological tissue. Moreover, it is possible to simplify and shorten time for an examination of observing time change of a biological tissue.

In a third aspect of the present invention, a medical image-processing apparatus comprising: an image data generator configured to generate image data of an MPR image, based on volume data of a biological tissue generated by an ultrasound diagnostic apparatus; a memory configured to store cross-sectional-position information showing a cross-sectional position of the MPR image; a display part; and a controller configured to: control the image data generator so as to, based on cross-sectional-position information of an MPR image from volume data generated on a first date, and volume data generated on a second date, generate image data of an MPR image of the second date in a cross-sectional position shown in cross-sectional information of the first date; and cause the display part to display an MPR image of the second date.

According to the third aspect, it is possible to, based on a cross-sectional position shown in cross-sectional-position information of a first date, and volume data of a second date, generate and display an MPR image of the second time in the cross-sectional position of the first date. Consequently, it is possible to easily obtain a tomographic image of the same cross section of a biological tissue, in an examination of observing time change of the biological tissue. Moreover, it is possible to simplify and shorten time for an examination of observing time change of a biological tissue.

In a fifth aspect of the present invention, a medical image-processing apparatus that processes volume data generated by an ultrasound diagnostic apparatus for each of a plurality of phases in a stress echocardiography examination of a biological tissue, comprising: an image data generator configured to generate image data of an MPR image, based on the volume data; a memory configured to store cross-sectional-position information showing a cross-sectional position of the MPR image; a display part; and a controller configured to: in a case where a second phase examination is performed after a first phase examination, control the image data generator so as to, based on cross-sectional-position information obtained at the time of generation of image data of an MPR image of the first phase, and volume data of each of the first phase and the second phase, generate image data of an MPR image of each of the first phase and the second phase in a cross-sectional position shown in cross-sectional-position information of the first phase; and cause the display part to display an MPR image of the first phase and an MPR image of the second phase side by side.

According to the fifth aspect, it is possible to, based on cross-section-position in formation of a first phase, and volume data of each of the first phase and a second phase, generate an MPR image of each of the first phase and the second phase in a cross-sectional position of the first phase, and display these MPR images side by side. Consequently, it is possible to easily obtain a tomographic image of the same cross section of a biological tissue, in a stress echocardiography examination of the biological tissue. Moreover, it is possible to simplify and shorten time for a stress echocardiography examination.

BRIEF DESCRIPTION OF THE DRAWINGS

FIG. 1 is a schematic block diagram illustrating an example of the entire configuration for an embodiment of an ultrasound diagnostic apparatus according to the present invention.

DETAILED DESCRIPTION OF THE EMBODIMENTS

Figure 2A:
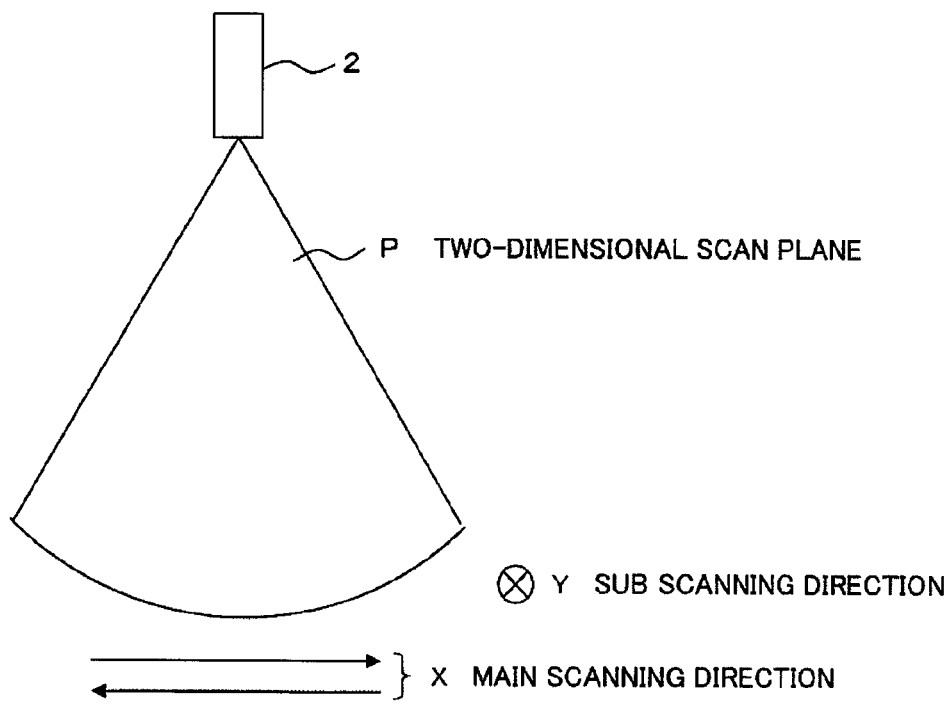
FIG. 2A and FIG. 2B are schematic explanatory diagrams for explaining an example of an ultrasonic scanning mode in an embodiment of an ultrasound diagnostic apparatus according to the present invention.

An embodiment of an ultrasound diagnostic apparatus and a medical image-processing apparatus according to the present invention will be described in detail with reference to drawings.

First Embodiment

FIG. 1 illustrates an example of the entire configuration for the first embodiment of an ultrasound diagnostic apparatus according to the present invention. An ultrasound diagnostic apparatus 1 is an apparatus that is used, for example, for obtaining an image showing the shape of biological tissue such as a heart and an image showing a blood flow condition.

[Apparatus Configuration]

The ultrasound diagnostic apparatus 1 comprises a two-dimensional ultrasonic probe 2, a transceiver 3, a signal processor 4, an image processor 5, an information memory 6, an image data memory 7, a user interface 8, and a controller 9. Specific examples for each part composing the ultrasound diagnostic apparatus 1 will be described below.

User Interface and Controller

First, the user interface 8 and the controller 9 will be described hereunder. A display part 81 and an operation part 82 are provided in the user interface 8.

The display part 81 corresponds to an example of a "display part" in the present invention. The display part 81 is composed of any display device such as an LCD (Liquid Crystal Display) and a CRT (Cathode Ray Tube).

The display part 81 displays various images such as an ultrasonic image obtained by the ultrasound diagnostic apparatus 1. Additionally, the display part 81 displays various kinds of information such as DICOM (Digital Imaging and Communications in Medicine) supplemental information about the image.

The operation part 82 is composed of any operational device or input device, such as a mouse, a trackball, a joystick, a control panel and a keyboard. The operation part 82 is used as an example of an "operation part" in the present invention.

The controller 9 comprises a microprocessor such as a CPU, and a storage unit such as a memory and a hard disk drive. The storage unit stores a control program 91 beforehand. The microprocessor operates based on the control program 91, and thus causes the ultrasound diagnostic apparatus 1 to execute operations that are characteristic of the present invention.

Thus, the controller 9 causes the display part 81 to display an image and a screen. Additionally, the controller 9 causes the ultrasound diagnostic apparatus 1 to execute an operation in response to a control signal transmitted from the operation part The controller 9 functions as an example of a "controller" for the present invention.

Two-Dimensional Ultrasonic Probe

The two-dimensional ultrasonic probe 2 (may simply be referred to as an ultrasonic probe 2) is provided with a plurality of ultrasonic transducers. The plurality of ultrasonic transducers are arranged two-dimensionally (e.g., in a matrix state (lattice-like state)) (an illustration thereof is omitted). The plurality of ultrasonic transducers are individually driven by the transceiver 3 to transmit the ultrasound. Additionally, the plurality of ultrasonic transducers receive the ultrasound reflected by the biological tissue.

Figure 2B:
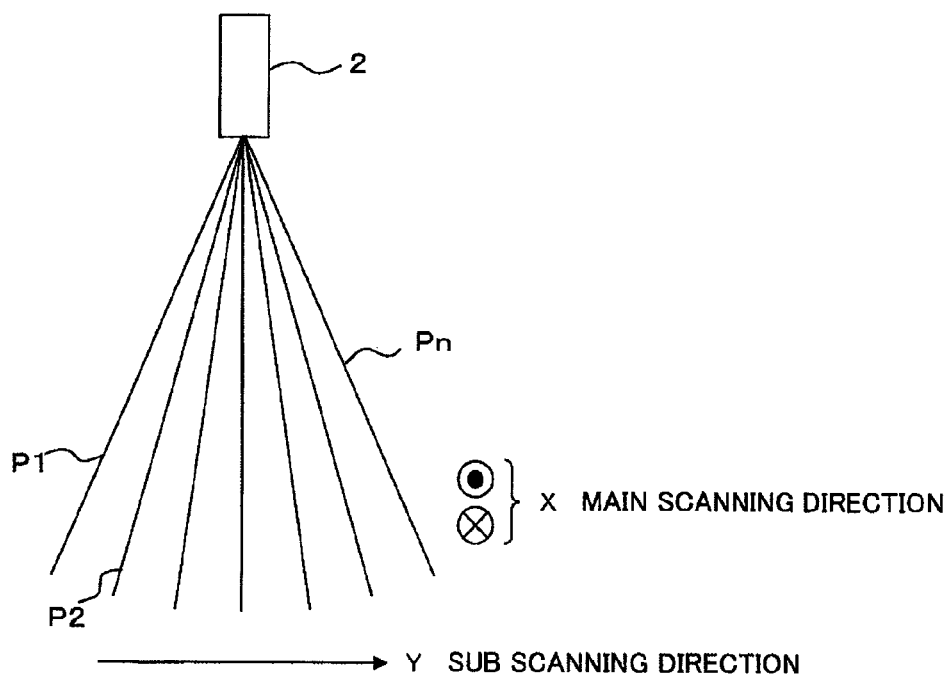
Figure 3:
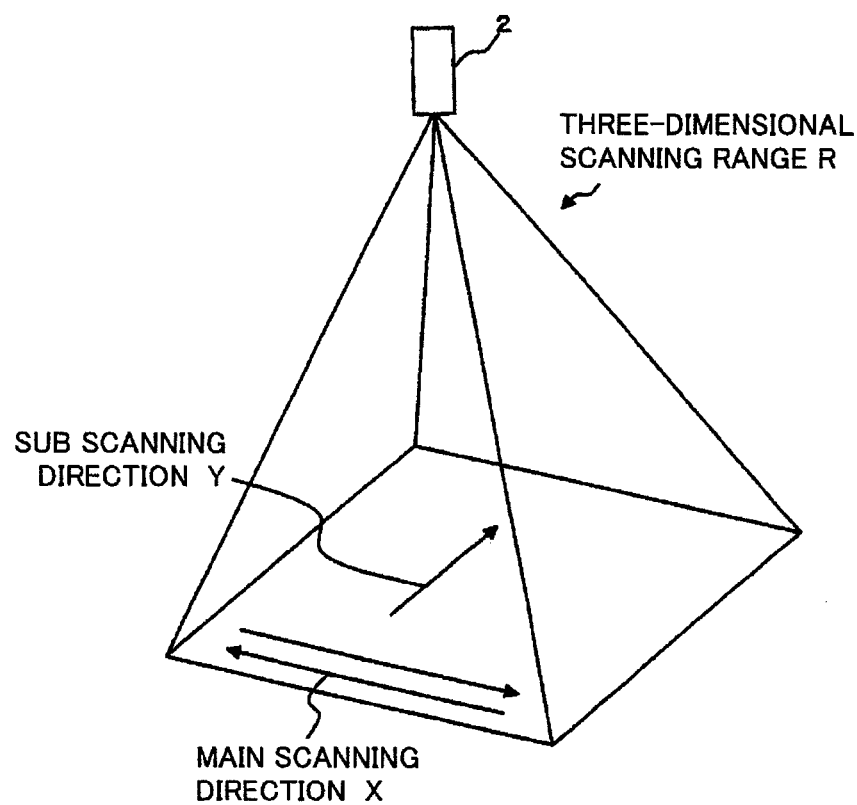
FIG. 3 is a schematic explanatory diagram for explaining an example of an ultrasonic scanning mode in an embodiment of an ultrasound diagnostic apparatus according to the present invention.
Figure 4:
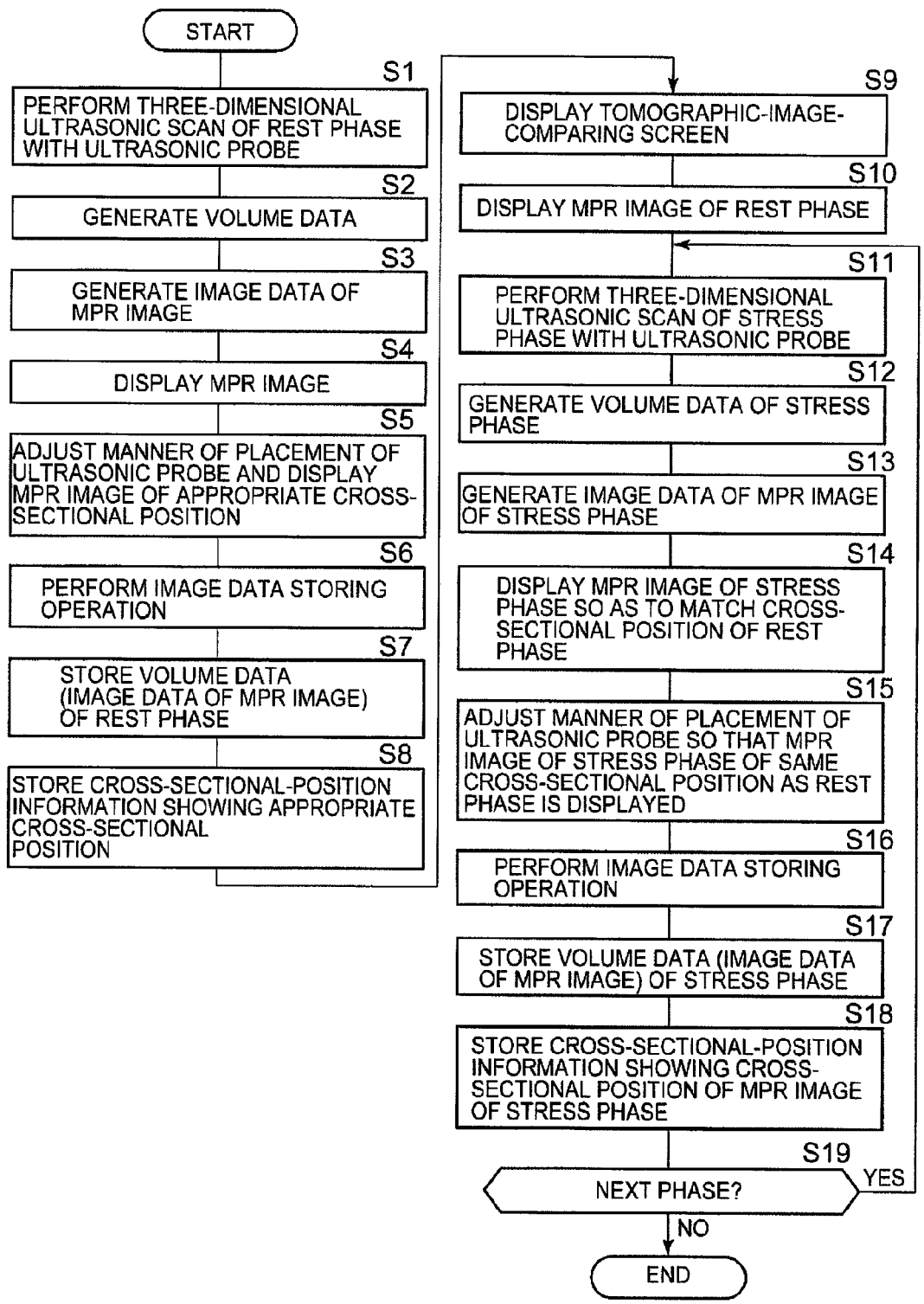
FIG. 4 is a flow chart illustrating an example of an operation mode in an embodiment of an ultrasound diagnostic apparatus according to the present invention.

FIGS. 2A, 2B and FIG. 3 illustrate an ultrasonic scanning mode performed by the two-dimensional ultrasonic probe 2. As shown in FIG. 2A, the ultrasonic probe 2 scans an ultrasonic beam transmitted from the arrangement surface of the ultrasonic transducers in the main scanning direction X. Thus, a two-dimensional scan plane P is formed in a radial pattern (in a fan shape). Additionally, the ultrasonic probe 2 scans the ultrasound in the sub scanning direction Y that is orthogonal to the main scanning direction X, and thereby sequentially forms a plurality of fan-shaped two-dimensional scan planes P1, P2, . . . and Pn, which are arranged in the sub scanning direction Y as shown in FIG. 2B. As described above, the ultrasonic probe 2 transmits while three-dimensionally scanning the ultrasound to form a three-dimensional scanning range R shown in FIG. 3.

A cross-sectional position for a tomographic image (B-mode image) obtained by the ultrasound diagnostic apparatus is generally determined by the relative position of the ultrasonic probe or the scanning origin with respect to the biological tissue. In other words, if the position of the ultrasonic probe or scanning origin changes, the tomographic image of the cross-sectional position corresponding thereto will be obtained.

Transceiver

The transceiver 3 comprises a transmission part for supplying an electrical signal to the ultrasonic probe 2 and transmitting ultrasound. Additionally, the transceiver 3 comprises a receiving part for receiving echo signals (reception signals), which are outputted from the ultrasonic probe 2 that has received a reflected wave of this ultrasound (both illustrations are omitted).

The transmission part of the transceiver 3 comprises a clock-signal-generating circuit, a transmission delay circuit, a pulse circuit, etc., which are not shown in the figure. The clock-signal-generating circuit generates a clock signal that determines the transmission timing and transmission frequency of the ultrasound. The transmission delay circuit performs transmission focus by imposing a delay when transmitting the ultrasound. The pulse circuit incorporates pulse generators, the number of which is equivalent to the number of individual channels corresponding to each ultrasonic transducer. That will cause the pulse circuit to generate a drive pulse at a transmission timing at which the delay is imposed and then supply it to each ultrasonic transducer of the ultrasonic probe 2.

Furthermore, the receiving part of the transceiver 3 comprises a pre-amplifier circuit, an A/D conversion circuit, and a reception delay/addition circuit, which are not shown in the figure. The pre-amplifier circuit amplifies, for every reception channel, echo signals outputted from each transducer of the ultrasonic probe 2. The A/D conversion circuit converts the amplified echo signals from A (analog) to D (digital). The reception delay/addition circuit applies the delay time necessary for determination of the reception tendency to the A/D-converted echo signals, and performs addition. This addition process will emphasize a reflection component from the direction according to the reception tendency. In some cases, a signal after the addition process may be referred to as "RF data (raw data)." The transceiver 3 inputs the RF data that has been obtained in this way into the signal processor 4.

Signal Processor

The signal processor 4 visualizes the amplitude information of the echo signal, based on the RF data having been inputted from the transceiver 3. The data generated by the signal processor 4 is transmitted to the controller 9 to be displayed on the display part 81 of the user interface 8, or inputted into the image processor 5. The signal processor 4 mainly comprises a B-mode process or 41, a Doppler processor 42, and a CFM processor 43.

(B-Mode Processor)

The B (Brightness) mode processor 41 generates B-mode ultrasound raster data, based on the RF data. In concrete, the B-mode processor 41 performs a band-pass filter process on the RF data, detects an envelope of the output signal thereof, and compresses this detected data by a logarithmic transformation. Thus, with respect to the respective two-dimensional scan planes P1 to Pn, image data of the tomographic image in which the signal strength is expressed by brightness is generated.

(Doppler Processor)

The Doppler processor 42 generates blood flow information by a pulse Doppler method (PW Doppler method), a continuous wave Doppler method (CW Doppler method) or the like. These methods are selectively applied, for example, by operating the operation part 82 of the user interface 8.

In the pulse Doppler method, a shift of frequency of the ultrasound (Doppler shift frequency component) arising from the Doppler effect caused by blood flow at a certain depth (distance from the ultrasonic probe 2) is detected using a pulse wave. Thus, the pulse Doppler method has a good distance resolution, and therefore is preferably used for depth measurement of tissue and blood flow for a specified site.

In a case where the pulse Doppler method is applied, the Doppler processor 42 extracts, with respect to the RF data inputted from the transceiver 3, the Doppler shift frequency component by performing a phase detection of the signals at a specified size of blood-flow observation range. Additionally, the Doppler processor 42 performs FFT (Fast Fourier Transformation) and then generates data showing the Doppler frequency distribution that represents the blood velocity in the blood-flow observation range.

Meanwhile, in the case of the continuous wave Doppler method, signals superposed with the Doppler shift frequency components for all sites in the transmission/reception direction of the ultrasound (radial direction in the two-dimensional scan plane P) are obtained using a continuous wave. These signals are signals that reflect all blood flow conditions in the path of the ultrasound. The continuous wave Doppler method has the merit that the speed of the measurement is excellent.

In a case where the continuous Doppler method is applied, the Doppler processor 42 extracts, with respect to the RF data that is inputted from the transceiver 3, the Doppler shift frequency component by performing phase detection on the signals received in a sample line of blood-flow observation. Additionally, the Doppler processor 42 performs FFT (Fast Fourier Transformation) and then generates data showing a Doppler frequency distribution that represents the blood velocity in the sample line.

(CFM Processor)

The CFM (Color Flow Mapping) processor 43 operates when a color flow mapping method is performed. The color flow mapping method is a method for displaying at real-time in a color format by superposing the blood flow information of the biological tissue on a B-mode image having a binary format. Examples of the blood flow information include the velocity, distribution, and strength of blood flow. The blood flow information is obtained as binary format information. It should be noted that "real-time" allows for a time lag to the extent that the ultrasonic image based on the ultrasonic scan can be obtained while the ultrasonic probe 2 is placed on the subject.

The CFM processor 43 comprises a phase detection circuit, a MTI (Moving Target Indication) filter, an autocorrelator, and a flow speed/variance operator. The CFM processor 43 separates a shape signal reflecting the shape of the biological tissue and a blood flow signal reflecting the blood flow, by means of a high-pass filter process (MTI filter process). Additionally, the CFM processor 43 calculates information such as the velocity, distribution and strength of blood flow for a plurality of positions by performing an autocorrelation process. In some cases, the CFM processor 43 may perform a non-linear process to reduce the shape signal.

Image Processor

The image processor 5 performs various kinds of image processing based on data generated by the signal processor 4. For example, the image processor 5 has a DSC (Digital Scan Converter). The DSC converts the data synchronized with the ultrasonic scan having been generated by the signal processor 4, into data used for display (TV scan mode data). This process is called a scan conversion process.

Additionally, the image processor 5 is provided with a volume data generator 51 and an MPR processor 52, which will be described below.

(Volume Data Generator)

The volume data generator 51 generates volume data (voxel data) by interpolating the image data of two-dimensional scan planes P1 to Pn generated by the B-mode processor 41. The volume data generator 51 comprises, for example, a DSC and a microprocessor.

In the case of display of a quasi three-dimensional image based on the volume data, the image processor 5 generates image data for display by performing image-processing such as a volume rendering process and an MIP (Maximum Intensity Projection) process. The controller 9 causes the display part 81 to display the quasi three-dimensional image based on the image data for display.

(MPR Processor)

The MPR (Multi-Planar Reconstruction) processor 52 generates image data for a tomographic image (an MPR image) in an arbitrary cross-sectional position of the biological tissue by converting a cross-section of the volume data generated by the volume data generator 51. The MPR processor 52 comprises, for example, a DSC and a microprocessor.

As described above, the signal processor 4 (the B-mode processor 41 thereof) and the image processor 5 generate image data for the tomographic image (MPR image based on the volume data) of the biological tissue, based on the results (data outputted from the transceiver 3) of the ultrasound received by the ultrasonic probe 2. The signal processor 4 and the image processor 5 correspond to an example of an "image data generator" in the present invention.

Information Memory

The information memory 6 stores cross-sectional-position information D showing the cross-sectional position of the MPR image. The information memory 6 corresponds to an example of a "storage part" in the present invention. The cross-sectional position indicated in the cross-sectional-position information D is expressed, for example, by using a three-dimensional coordinate system defined in the volume data.

The cross-sectional-position information D is stored so as to be associated with patient identification information such as a patient ID. The controller 9 is capable of searching the intended cross-sectional-position information D by using the patient identification information as a search key. Additionally, the cross-sectional-position information D is also associated with examination date information showing the date (and time) of generation of the image data of the MPR image. The examination date information is used as a search key when the cross-sectional-position information D is searched based on the examination date.

The information memory 6 comprises a storage unit such as a memory and a hard disk drive. The microprocessor or the like (controller 9) performs a process of writing/reading data in/out of the information memory 6.

Image Data Memory

The image data memory 7 stores various kinds of image data such as volume data V generated by the volume data generator 51 and the image data for the MPR image. Additionally, various data such as the DICOM supplemental information for the image data is also stored in the image data memory 7.

The image data memory 7 comprises a comparatively high-capacity storage unit, examples of which are memory such as a DRAM (Dynamic Random Access Memory) and a hard disk drive. The microprocessor or the like (controller 9) performs a process of writing/reading data in/out of the information memory 7.

[Usage]

An example of a usage of an ultrasound diagnostic apparatus 1 will be described with reference to FIG. 4 to FIG. 7.

The usage for a case of stress echocardiography of a heart will be described hereunder. Stress echo cardiography is an examination for observing how the motion (function) of a cardiac muscle has changed by stress applied to the subject. Accordingly, as described above, with respect to phases before and after stress is applied (or each phase of the stress), it is important to comparatively observe the same section of the cardiac muscle by obtaining images of the same cross-sectional position of the heart.

The usage for obtaining (almost) the same cross-sectional position of the heart in the case of examination in the resting phase and examination in a stress phase will be described hereunder. The resting phase means a condition in which the subject is not subjected to stress such as motion or medication. The stress phase means a condition in which the subject is subjected to stress.

Examination in the Resting Phase

First, examination in the resting phase is performed. For that, a coupling medium such as an ultrasound jelly is applied to the body surface of the subject and the ultrasound-outputting surface of the ultrasonic probe 2. Then, an ultrasonic three-dimensional scan is performed with the ultrasonic probe 2 placed on the body surface located adjacent to an apex of the heart (S1). Such a manner of placement of the ultrasonic probe 2 is called an apical approach.

The results received by the ultrasonic probe 2 are transmitted to the B-mode processor 41 through the transceiver 3. The B-mode processor 41 generates image data for the tomographic image, based on data having been inputted from the transceiver 3. Thus, the image data for the tomographic image in each of the two-dimensional scan planes P1, P2, . . . and Pn shown in FIG. 2B can be obtained.

The volume data generator 51 generates the volume data based on the image data (S2). The volume data is stored, for example, in the image data memory 7.

Here, Steps S1 and S2 are repeated at specified time intervals. That enables the volume data to be obtained at specified time intervals (frame rate). The volume data stored in the image data memory 7 includes a plurality of sets of volume data obtained at the frame rate.

The MPR processor 52 generates image data for the MPR image based on the volume data (S3). The controller 9 causes the display part 81 to display this MPR image (S4). In some cases, the image data of the MPR image can be directly generated from data obtained by a three-dimensional scan shown in Step S1.

In Step S3, the MPR images at a plurality of different cross-sectional positions of the heart can be displayed. Additionally, because an apical approach using the three-dimensional ultrasound scan (volume scan) is performed in this usage, it is possible (in principle) to obtain and display the MPR image for an optional cross-sectional position of the heart. This makes it possible to display, for example, the MPR image for a short-axis view of the left ventricle that is optimum for evaluation of heart wall motion at any level (an arbitrary position (depth) in the direction of connecting the apex and base).

In Steps S3 and S4, the MPR processor 52 sequentially generates image data for the MPR image in the specified cross-sectional position, based on the volume data obtained at the specified frame rate, and further, the controller 9 causes the display part 81 to display, at the specified frame rate, the sequentially generated MPR images.

Here, a user specifies a desired cross-sectional position by operating the operation part 82 when needed. The MPR processor 52 generates image data for the MPR image in the cross-sectional position specified by the user, based on the volume data obtained at the specified frame rate. The controller 9 causes the display part 81 to display the sequentially generated MPR images. This makes it possible to display, on the display part 81, a moving image (specified frame rate) of the MPR image for the heart in the cross-sectional position specified by the user.

Figure 5:
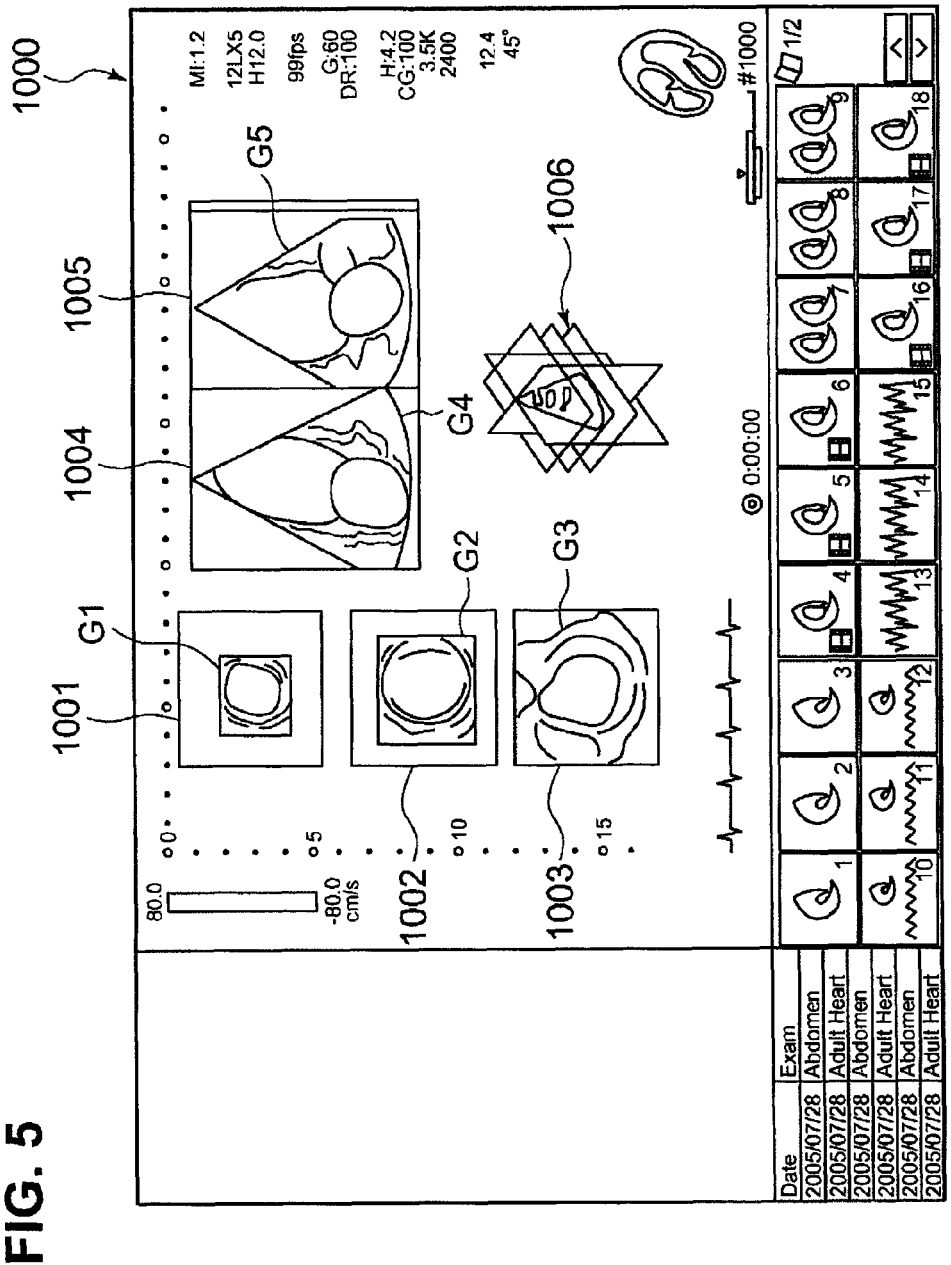
FIG. 5 is a schematic diagram illustrating an example of a display screen that is displayed by an embodiment of an ultrasound diagnostic apparatus according to the present invention.

FIG. 5 illustrates an example of a display mode of the MPR image in Step S4. A plurality of MPR images are displayed on a tomographic image display screen 1000. Five display ranges 1001 to 1005 are provided in this tomographic image display screen 1000. An MPR image is displayed on each of the display ranges 1001 to 1005.

The display ranges 1001, 1002 and 1003, which are arranged in the vertical direction of the screen, respectively display moving images G1, G2 and G3 of the MPR image for a short-axis view of the left ventricle at an apex level, a papillary muscle level and a base level.

Here, the cross-sectional position and the number of the MPR image displayed on the tomographic image display screen 1000 are preferably set so that sites (segments) recommended by ASE (American Society of Echocardiography) are all included. Alternatively, in order to observe the heart in more detail than that, the MPR images in more cross-sectional positions can also be displayed by setting, for example, sixteen cross-sectional positions of the heart.

Additionally, on the tomographic image display screen 1000, in addition to the above MPR images G1 to G3, moving images G4 and G5 of the MPR images of an apical four-chamber view and an apical two-chamber view are respectively displayed in the display ranges 1004 and 1005.

The user can change each of the cross-sectional positions of the MPR images displayed in each of the display ranges 1001 to 1005 by moving the cross-sectional positions shown in an operation part 1006 of changing the cross-sectional position, which is displayed under the display ranges 1004 and 1005 by means of the operation part 82. The operation is performed, for example, by dragging a plane in the figure showing the cross-sectional positions to a desired cross-sectional position.

Additionally, the user causes the moving images of the cross-sectional position (in particular, moving images G1, G2 and G3 of a short-axis view of the left ventricle) in which the heart wall motion can be adequately observed to be displayed by adjusting the manner of placement of the ultrasonic probe 2 on the subject while observing the MPR images displayed on the tomographic image display screen 1000 (S5).

Upon displaying the moving images of the appropriate cross-sectional position, the user performs a predetermined operation for storing the image data with the operation part 82 (S6). Examples of this operation include double-click of a mouse. Once this operation is performed, the controller 9 stores, in the image data memory 7, the volume data for the specified frame rate that is the basis of the moving images as volume data V1 for the resting phase (S7).

Instead of storing the volume data V1, it is possible to configure so as to store the image data for the moving images G1 to G5 of the MPR images, which are respectively displayed in the display ranges 1001 to 1005. Additionally, it is also possible to configure so as to store both the volume data V1 and the image data for the moving images G1 to G5.

Furthermore, the controller 9 stores, in the information memory 6, the cross-sectional-position information D1 showing the appropriate cross-sectional position in the resting phase (S8). The cross-sectional-position information D1 includes, for example, the cross-sectional positions of the moving images G1 to G5 of the MPR images, which are displayed in the respective display ranges 1001 to 1005. Each cross-sectional position is shown, for example, in the three-dimensional coordinate system defined in the volume data V1. This is the end of the examination in the resting phase.

Examination in a Stress Phase

Subsequently, examination in the stress phase will be performed. For that, the user firstly causes the display part 81 to display a screen that displays the MPR image of the stress phase, such as a tomographic-image-comparing screen 2000 shown in FIG. 6 (S9).

Figure 6:
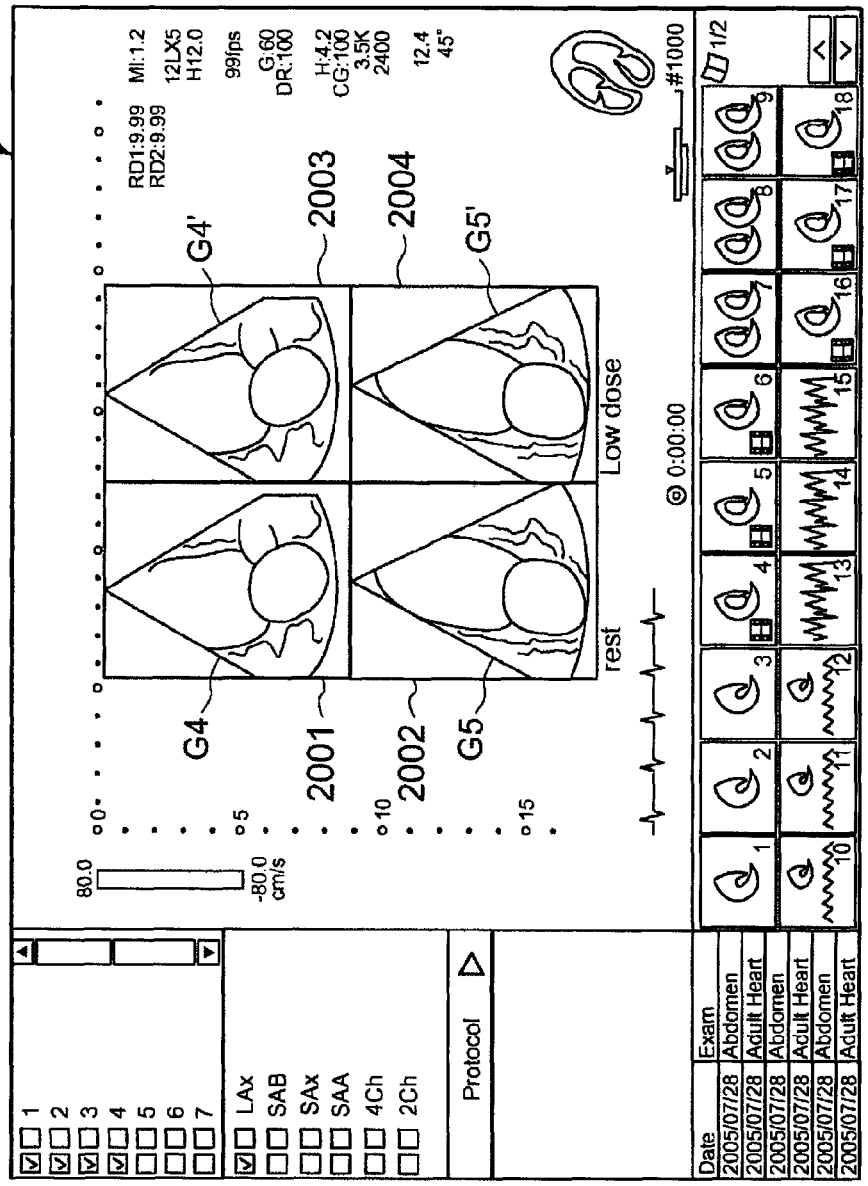
FIG. 6 is a schematic diagram illustrating an example of a display screen that is displayed by an embodiment of an ultrasound diagnostic apparatus according to the present invention.

The display ranges 2001 to 2004 are provided in the tomographic-image-comparing screen 2000. The display ranges 2001 to 2004 display images of two different phases side by side. In FIG. 6, the MPR images of the resting phase are respectively displayed in the display ranges 2001 and 2002, and the MPR images of the stress phase are respectively displayed in the display ranges 2003 and 2004.

The controller 9 reads out the volume data V1 for the resting phase stored in Step S7 from the image data memory 7 and transmits to the MPR processor 52. Additionally, the controller 9 transmits, to the MPR processor 52, the cross-sectional-position information D1 stored in Step S8.

The MPR processor 52 generates image data of the MPR images of the resting phase, based on the volume data V1 and the cross-sectional-position information D1. The controller 9 causes the tomographic-image-comparing screen 2000 to display the MPR images of the resting phase, based on the generated image data (S10).

In the display ranges 2001 and 2002 shown in FIG. 6, the moving images G4 and G5 of the MPR image of an apical four-chamber view and an apical two-chamber view are respectively displayed as an example of a display mode. The displayed images are not necessarily moving images but may be still images at a certain phase of a heartbeat.

Additionally, the MPR image based on the volume data V1 is displayed in the above Step S10, but it is not limited to this. For example, in the case of storing the image data for the MPR image in Step S7 and displaying this MPR image in Step S10, it is possible to display, for example, the MPR image at the cross-sectional position specified by the user selectively in the display ranges 2001 and 2002.

The user applies an ultrasound jelly or the like when needed in order to obtain the images of the heart to which the stress is applied, and places the ultrasonic probe 2 on the body surface located near an apex of the heart for performing the ultrasonic three-dimensional scan (S11).

The results received by the ultrasonic probe 2 are transmitted to the B-mode processor 41 through the transceiver 3, whereby image data for the tomographic image is generated. Furthermore, the volume data generator 51 generates volume data based on these sets of image data for the tomographic images (S12). Steps S11 and S12 are repeated at specified time intervals in the same way as Steps S1 and S2. That enables the volume data to be obtained at specified frame rate.

The MPR processor 52 generates image data for the MPR images (in this case, an apical four-chamber view and an apical two-chamber view) in the cross-sectional positions shown in the cross-section information D1, based on the volume data and the cross-sectional-position information D1 (S13). The controller 9 causes the tomographic-image-comparing screen 2000 to display the MPR images of the apical four-chamber view and the apical two-chamber view (S14).

Consequently, as illustrated in FIG. 6, in the display ranges 2003 and 2004 of the tomographic-image-comparing screen 2000, moving images G4' and G5' for the MPR images of the apical four-chamber view and the apical two-chamber view in the stress phase are displayed at real time at the specified frame rate. The MPR images G4' and G5' respectively have cross-sectional positions matched with the cross-sectional positions of the MPR images G4 and G5 for the resting phase.

In FIG. 6, the display range 2001 and the display range 2003 are placed side by side, and the display range 2002 and the display range 2004 are placed side by side.

The display range 2001 displays the MPR image (moving image) G4 of the apical four-chamber view in the resting phase, and the display range 2003 displays the MPR image (moving image) G4' of the apical four-chamber view in the stress phase. That enables the user to easily perform a comparative observation of the MPR images G4 and G4' of the apical four-chamber view, which are obtained in different phases.

Further, the display range 2002 displays the MPR image (moving image) G5 of the apical two-chamber view in the resting phase, and the display range 2004 displays the MPR image (moving image) G5' of the apical two-chamber view in the stress phase. That enables the user to easily perform a comparative observation of the MPR images G5 and G5' of the apical two-chamber view, which are obtained in different phases.

Here, the user adjusts the manner of placement of the ultrasonic probe 2 on the subject as needed so that the cross-sectional position of the MPR image G4' of the apical four-chamber view coincides with the cross-sectional position of the MPR image G4 of the apical four-chamber view (or so that the cross-sectional position of the MPR image G5' of the apical two-chamber view coincides with the cross-sectional position of the MPR image G5 of the apical two-chamber view). In other words, the user adjusts the manner of placement of the ultrasonic probe 2 so that the MPR images having (almost) the same cross-sectional position can be displayed in the display range 2001 and 2003, while comparative observation the images displayed in the display ranges 2001 and 2003 (S15).

As described above, once one cross-sectional position is matched, other cross-sectional positions (an apical two-chamber view, and a short-axis view of the left ventricle at an apex level, at a papillary muscle level, and at a base level) are also matched. It is necessary at this moment to keep the positional relation between two cross sections not to change.

Once the cross-sectional position of the MPR image G4' in the stress phase, which is real-time displayed, matches the cross-sectional position of the MPR image G4 in the resting phase, the user performs an operation of requesting storage of the image data (S16). Once this operation is performed, the controller 9 stores, in the image data memory 7, volume data V2 in the stress phase that is real-time generated at the specified frame rate (S17).

Here, instead of storing the volume data V2, it is possible to configure so as to display the image data of the moving images G4' and G5' of the MPR images, which are respectively displayed in the display ranges 2003 and 2004. Additionally, it is also possible to configure so as to store both the volume data V2 and the image data of the moving images G4' and G5'.

Additionally, the controller 9 stores, in the information memory 6, cross-sectional-position information D2 showing the cross-sectional position of the MPR image in the stress phase (S18). The cross-sectional-position information D2 includes, for example, the cross-sectional positions of the moving images G4' and G5' of the MPR images, which are displayed in the display ranges 2003 and 2004. This cross-sectional position is shown, for example, in the three-dimensional coordinate system defined in the volume data V2.

If there is a next phase (e.g., higher-stress phase) (S19; Y), the above steps S11 to S18 will be repeated. In this next phase, the MPR image for a phase (e.g., the previous phase) other than the resting phase can be displayed with the MPR image for the next stress phase. After observation for all phases are completed (S19; N), the examination in the stress phase ends.

The number of examinations in the stress phase is accordingly determined depending on the stress amount and the clinical condition of the biological tissue intended for observation, etc. Additionally, the number of examinations in the stress phase can also be determined beforehand, or accordingly determined depending on the intermediate examination results and the like.

In the stress phase examination as described above, cross-sectional positions for the MPR images of the apical four-chamber view or the apical two-chamber view are matched in the different phases by referring to the tomographic-image-comparing screen 2000. However, other MPR images, such as the MPR image of a short-axis view of the left ventricle can also be used for matching the cross-sectional positions.

Figure 7:
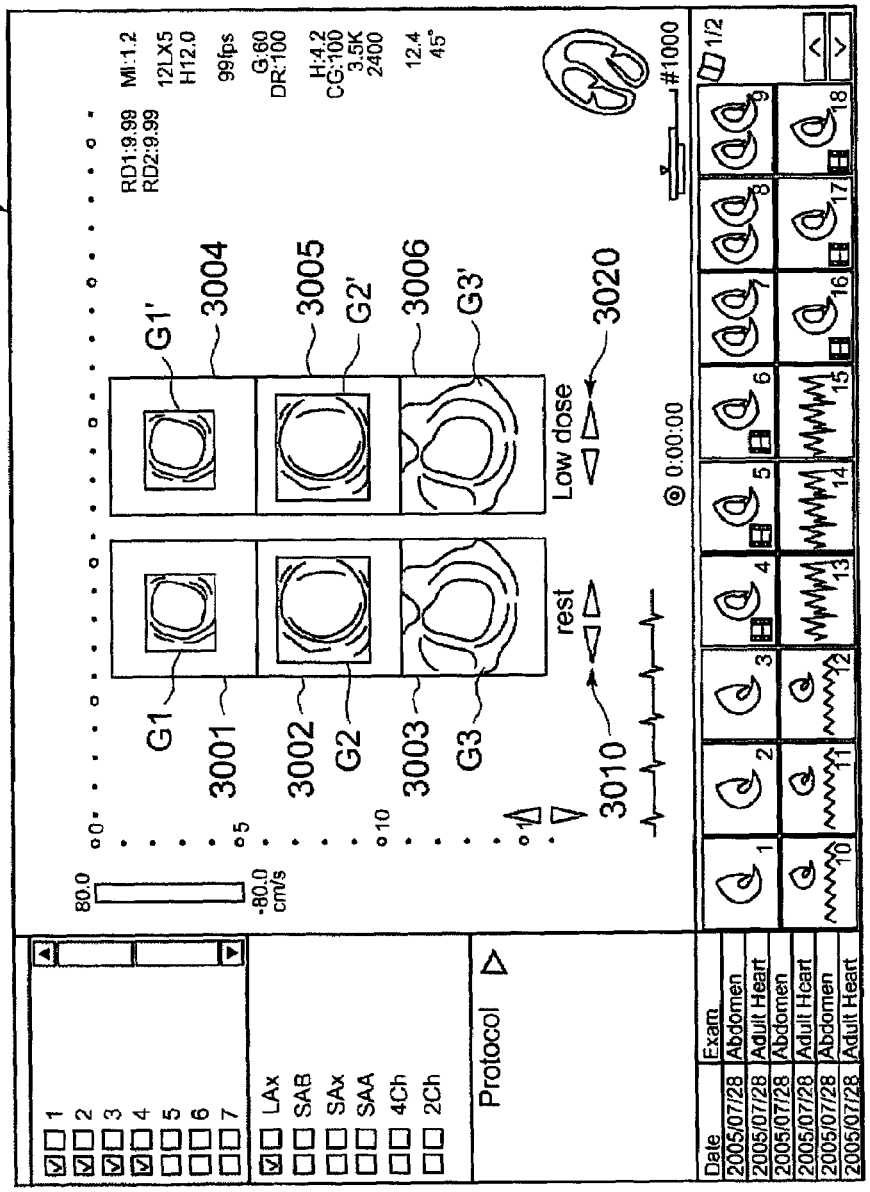
FIG. 7 is a schematic diagram illustrating an example of a display screen that is displayed by an embodiment of an ultrasound diagnostic apparatus according to the present invention.

FIG. 7 is an example of a tomographic-image-comparing screen 3000 for comparative observation of the MPR images of a short-axis view of the left ventricle. The tomographic-image-comparing screen 3000 includes display ranges 3001 to 3006, which display the MPR images.

The display ranges 3001 and 3004, which are placed side by side, respectively display the MPR images G1 and G1' of the short-axis view of the left ventricle at an apex level in the resting phase and in the stress phase. That enables the user to easily perform a comparative observation of the MPR images G1 and G1' of the short-axis view of the left ventricle at an apex level in the resting phase and in the stress phase. The MPR image G1' in the stress phase is generated from the volume data V2 based on the cross-sectional-position information D1. That results in that the MPR image G1' is an image for the cross-sectional position that matches the one of the MPR image G1 in the resting phase (the following are the same as above).

Similarly, the display ranges 3002 and 3005 respectively display the MPR images G2 and G2' for the short-axis view of the left ventricle at a papillary muscle level in the resting phase and in the stress phase. Additionally, the display ranges 3003 and 3006 respectively display the MPR images G3 and G3' for the short-axis view of the left ventricle at a base level in the resting phase and in the stress phase. That enables the user to easily perform a comparative observation of the MPR images G1 and G1' respectively for the short-axis view of the left ventricle at a papillary muscle level and at a base level in the resting phase and in the stress phase.

As in Step S15, the user can adjust the manner of placement of the ultrasonic probe 2 on the subject as needed so that the cross-sectional position of the MPR image G1' at an apex level is the same as the MPR image G1 (or so that the cross-sectional position of the MPR image G2' or G3' at a papillary muscle level or at a base level is the same as the MPR image G2 or G3).

Additionally, phase switching operation parts 3010 and 3020 are provided in the tomographic-image-comparing screen 3000. The phase switching operation parts 3010 and 3020 are operated for displaying the MPR images obtained in different phases. Examples of the stress phase include no stress (resting phase; the condition in which stress such as a drug is not applied), low stress (low dose; the condition in which stress such as a drug is low), and high stress (high dose; the condition in which stress such as a drug is high).

In the display condition shown in FIG. 7, once the user operates the phase switching operation part 3010 (clicks one of right and left direction arrows by mouse), the images displayed in the display ranges 3001, 3002 and 3003 are respectively switched from the MPR images G1, G2 and G3 in the resting phase into, for example, the MPR images G1', G2' and G3' for the low stress condition. This switching process of the display image is performed by the controller 9 having received a signal from the user interface 8 (the following are the same as above).

Additionally, in the display condition shown in FIG. 7, once the user operates the phase switching operation part 3020 (clicks one of right and left direction arrows with mouse), the images displayed in the display ranges 3004, 3005 and 3006 are respectively switched from the MPR images G1', G2' and G3' in the low stress condition into, for example, the MPR images G1", G2" and G3" (not shown) in the high stress condition.

In a case where the images of the same phase are displayed when the phase switching operation part 3010 or 3020 is operated and the displayed images are switched, images of different phases may be displayed by automatically switching the images displayed in the other side of the display range.

[Actions and Advantageous Effects]

Actions and advantageous effects of the ultrasound diagnostic apparatus 1 are described. When obtaining the image data for the tomographic image (MPR image) of biological tissue such as a heart, the ultrasound diagnostic apparatus 1 stores, in the information memory 6, the cross-sectional-position information D (D1) showing the cross-sectional position of that tomographic image. Additionally, when obtaining the image data for a new tomographic image of the biological tissue, the ultrasound diagnostic apparatus 1 obtains the image data for new tomographic image corresponding to the cross-sectional position shown in the cross-section location information D of the image data for the tomographic image having been obtained in the past and then displays this new tomographic image and the past tomographic image side by side.

In particular, in a case in which a stress echocardiography is performed by obtaining volume data from the three-dimensional ultrasonic scan, the ultrasound diagnostic apparatus 1 operates, based on the cross-sectional-position information D for the MPR image stored by the examination in the past phase, to display at real time the MPR image for the cross-section corresponding to the MPR image for this past phase.

According to the ultrasound diagnostic apparatus 1, in the examination for observing the time-elapsed changes in biological tissue, it is possible to automatically obtain the tomographic image for the cross-sectional position corresponding to the tomographic image observed in the past examination, and therefore easily obtain the tomographic images in the same cross-sectional position of the biological tissue. Examples of such examination include a stress echocardiography, an observation of the clinical course, a pre-treatment/post-treatment observation (periodical medical examination such as a prognostic follow-up), and a preoperative/postoperative observation.

Additionally, according to the ultrasound diagnostic apparatus 1, the tomographic image obtained in the past examination can be placed side by side with the tomographic image obtained in new examination in a condition in which the mutual cross-sectional positions are matched, which makes it possible to comparatively observe these images easily.

Additionally, the user can match the cross-sectional position of the new tomographic image with the cross-sectional position of the past tomographic image by simply adjusting the manner of placement of the ultrasonic probe 2 as needed. This makes it possible to easily perform an examination such as a stress echocardiography examination for observing the time-elapsed changes in biological tissue. It is also possible to shorten the examination time.

Furthermore, according to the ultrasound diagnostic apparatus 1, a plurality of pairs of the past tomographic image and the new tomographic image, which are matched with the cross-sectional position, can be simultaneously displayed as shown in FIG. 6 and FIG. 7. That enables the user to perform a comprehensive diagnosis, while comparative observation of the images of various cross-sectional positions of the biological tissues.

MODIFICATION EXAMPLES

It is possible to modify the ultrasound diagnostic apparatus 1 as described below.

Modification Example 1

In the above embodiment, the usage for the case of obtaining a new image at real time has been described, but it is not limited to this. For example, the present invention can also be applied to a case of comparative observation (review) of the images obtained at a plurality of different dates in the past (timing that is different in date or time).

In the case of comparison of the images obtained at two different dates, the image obtained at the earlier date may be referred to as a "past" image, where as the image obtained at the later date may be referred to as a "new" image.

Figure 8:
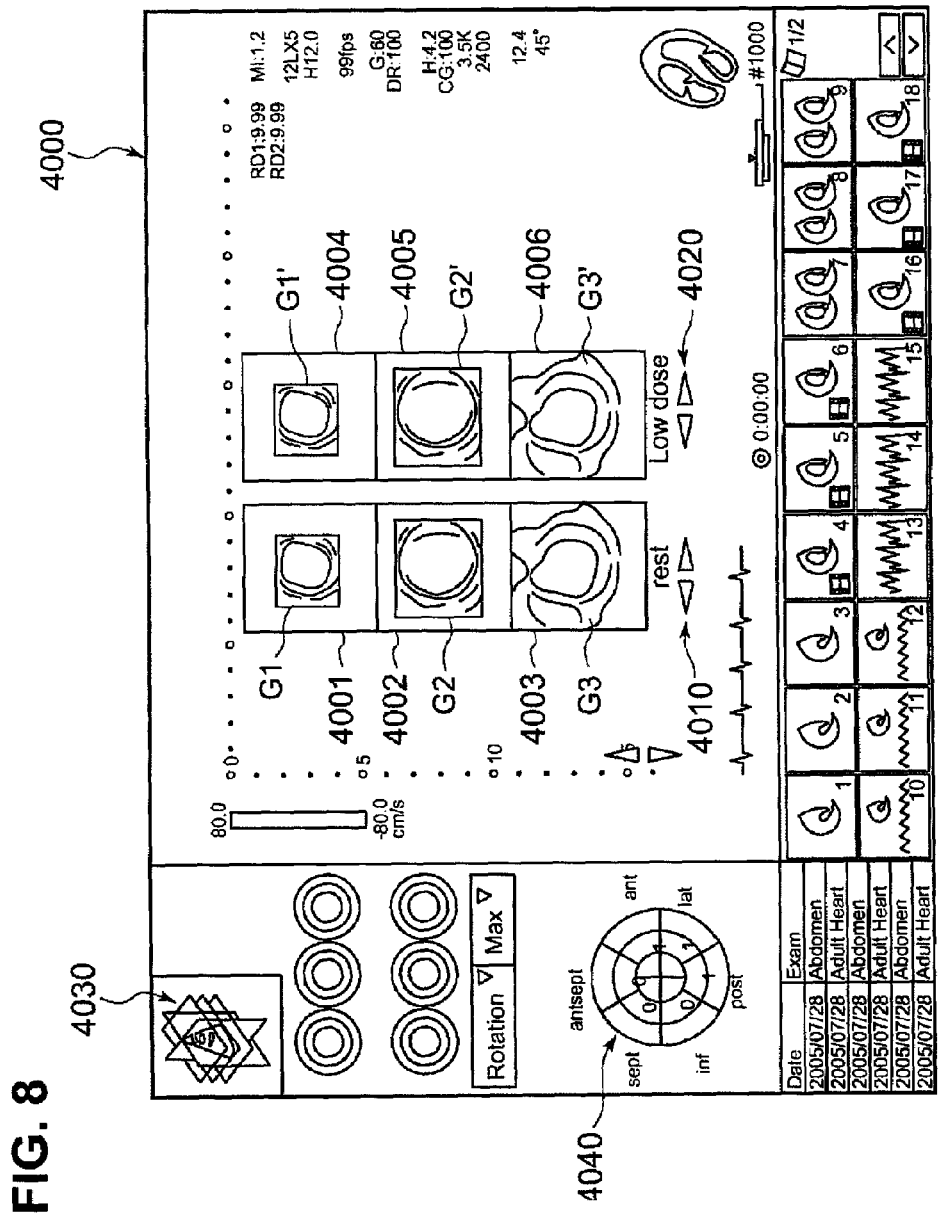
FIG. 8 is a schematic diagram illustrating an example of a display screen that is displayed by an embodiment of an ultrasound diagnostic apparatus according to the present invention.

Now, a review of the examination for observing the time-elapsed changes in biological tissue, such as stress echocardiography, is performed using, for example, a tomographic-image-comparing screen 4000 shown in FIG. 8. The tomographic-image-comparing screen 4000 includes display ranges 4001 to 4006 as in the case of the tomographic-image-comparing screen 3000 of FIG. 7. Additionally, the tomographic-image-comparing screen 4000 includes phase switching operation parts 4010 and 4020, which are similar to those in FIG. 7.

The display ranges 4001 and 4004 respectively display the MPR images G1 and G1' of a short-axis view of the left ventricle at an apex level in the resting phase and in the stress phase. The MPR images G1 and G1' are mutually matched in cross-sectional position, for example, in the same way as shown in Step S15 of FIG. 4.

Additionally, the display ranges 4002 and 4005 respectively display the MPR images G2 and G2' for a short-axis view of the left ventricle at a papillary muscle level in the resting phase and in the stress phase. The MPR images G2 and G2' are also mutually matched in the cross-sectional position.

The display ranges 4003 and 4006 respectively display the MPR images G3 and G3' for a short-axis view of the left ventricle at a base level in the resting phase and the stress phase. The MPR images G3 and G3' are also mutually matched in cross-sectional position.

In a case in which the volume data for each MPR image is stored, the user can adjust the cross-sectional position for the MPR image as needed. This adjustment operation is performed, for example, by specifying the MPR image intended for changing the cross-section through a click using a mouse, and further by dragging an operation part 4030 for changing cross-sectional position.

Additionally, in a case where the volume data for each MPR image is stored, once a pair of MPR images (e.g., MPR images G1 and G1') intended for a comparative observation are specified, and the operation part 4030 for changing cross-sectional position is operated, it is possible to change the cross-sectional positions of this pair of MPR images at one time.

This case will be described more specifically. For example, when the MPR images G1 and G1' are specified, and a new cross-sectional position is set by the cross-sectional-position change operation part 4030, the controller 9 transmits the content of the setting of the new cross-sectional position to the MPR processor 52. This content of the setting is information shown in a three-dimensional coordinate system defined in the volume data V1 and V2. Additionally, the controller 9 reads out the volume data V1 and V2 from the memory 7, and transmits them to the MPR processor 52. The MPR processor 52 generates image data for the MPR image of the new cross-sectional position, based on the volume data V1. Additionally, the MPR processor 52 generates image data for the MPR image of the new cross-sectional position, based on the volume data V2. The controller 9 causes the display range 4001 to display the MPR image for the new cross-sectional position in the resting phase, as well as causes the display range 4002 to display the MPR image for the new cross-sectional position in the stress phase, based on the image data generated from the MPR processor 52.

In this modification example, the MPR images in two different phases are displayed side by side, but it is also possible to display side by side the MPR images in three or more phases. In this case, it is possible to configure so that such one-time change for the cross-sectional position is performed at one time for the MPR images in all phases (a group of three or more MPR images intended for the comparison).

By enabling this one-time change of the cross-sectional position, the need for individually setting the desired cross-sectional position for each phase is eliminated, and therefore, it becomes possible to efficiently perform the reviewing operation in a shorter time.

Additionally, a polar map (may be referred to as a bull's eye) 4040 is displayed on the tomographic-image-comparing screen 4000. The polar map 4040, in which a three-dimensional heart is projected on a two-dimensional image, quantifies the motion state of a partial region of the heart, and represents the result of the quantification using a color distribution or numerical value. To quantify the motion state, it is possible to employ speckle tracking using MPR two-dimensional images or three-dimensional images.

Examples of the motion state of biological tissue (heart) represented by the polar map 4040 include displacement of the heart wall and displacement velocity, torsional motion and torsional motion velocity, shortening and shortening velocity, and strain of motion of the heart wall and strain rate, and relative rotation gradient.

The polar map 4040 represents, for example, the difference in numerical values showing the motion state for each partial region with respect to the MPR images of the two phases (in which the cross-sectional positions are matched) displayed on the tomographic-image-comparing screen 4000.

A polar map 4040 displayed based on the MPR image G1 and G1' will be described hereunder. The controller 9 quantifies the motion state for each partial region of each of the MPR images G1 and G1' by using the same method as the conventional one. Here, each partial region is shown in a three-dimensional coordinate system defined in the volume data V1 and V2. Additionally, the controller 9, for example, subtracts the numerical value of MPR image G1 from the numerical value of MPR image G1' with respect to each partial region. Then, the controller 9 displays the polar map 4040 in which this difference is represented by a color or a numerical value.

By using this polar map 4040, it is possible to quantitatively evaluate the changes in motion state of the cross-sectional position in different phases. This makes it possible to improve the reliability and effectiveness of diagnosis.

It may also be possible to quantitatively evaluate changes in motion state of the biological tissue by applying other methods. Examples of these methods include TDI (Tissue Doppler Imaging). TDI measures and two-dimensionally displays, in a color format, the velocity of motion exercised by a comparatively faster-moving biological tissue such as a heart wall.

According to the modification example described above, it is possible to automatically display side by side, the tomographic images in the same cross-sectional position, which have been obtained at different dates. This makes it possible to easily perform a comparative observation of the images in a review of the examination for observing the time-elapsed changes in biological tissue.

Because stress echocardiography examination for the heart is to observe how the motion of the cardiac muscle has changed according to the presence and amount of stress, the time-elapsed comparisons (comparison between phases) for the same cross-section of the heart is critical.

Modification Example 2

In the above embodiment, the case of real-time observation during three-dimensional scanning of the biological tissue with ultrasound has been described, but the present invention can also be applied to observation of biological tissue (heart) via an ECG-gated scan.

Figure 9:
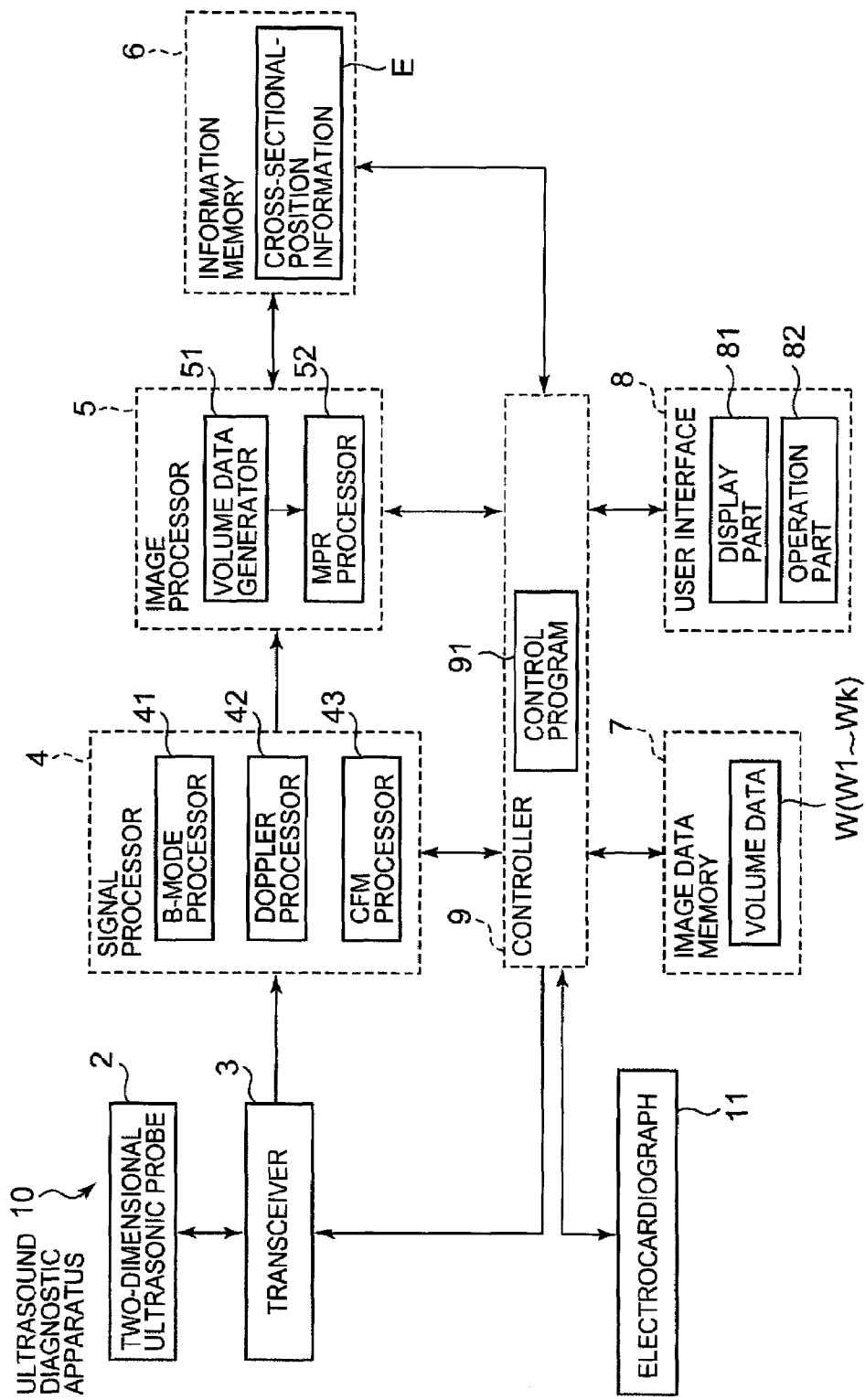
FIG. 9 is a schematic block diagram illustrating an example of the entire configuration in a modification example for an embodiment of an ultrasound diagnostic apparatus according to the present invention.

FIG. 9 illustrates a configuration example of an ultrasound diagnostic apparatus used for observation of biological tissue by ECG-gated scan. An ultrasound diagnostic apparatus 10 has a configuration in which an electrocardiograph 11 is added to the abovementioned ultrasound diagnostic apparatus 1.

The electrocardiograph 11 is a device for generating an electrocardiogram (ECG) that records the time-elapsed changes in electrical activities of the heart. The electrocardiogram provides information showing the time-elapsed changes in electrical activities of the heart. The electrocardiograph 11 has a plurality of electrodes attached to the body surface of the subject in the same manner as conventionally conducted. Further, the electrocardiograph 11 has a circuit for generating the electrocardiogram based on the time-elapsed changes in potential difference detected by the plurality of electrodes. The electrocardiogram generated by the electrocardiograph 11 is displayed on the display part 81 by the controller 9. The electrocardiograph 11 functions as one example of an "electrocardiogram generator" in the present invention.

Additionally, the controller 9 obtains a period T of the electrocardiogram inputted from the electrocardiograph 11. The period T is obtained by detecting the interval between an R wave and an adjacent R wave (R-R interval), for example. Furthermore, the controller 9 transmits, to the transceiver 3, a control signal according to the period T of the electrocardiogram.

The transceiver 3 drives the ultrasonic probe 2 based on this control signal to transmit the ultrasound. The ultrasonic probe 2 transmits the ultrasound while scanning in a circulative manner a plurality of partial regions of the heart at every period T of the electrocardiogram.

For example, in a case where the heart is divided into a number k of the partial regions Q1 to Qk (i=1 to k representing the order of scanning), the ultrasonic probe 2 operates so as to scan the partial region Q1 during the first one period T, scan the partial region Q2 during the next one period T . . . and, in this way, scan the last partial region Qk, and further, scan the first partial region Q1 during the next one period T.

The result of reception of the reflected ultrasonic waves sequentially received by the ultrasonic probe 2 is transmitted to the B-mode processor 41 through the transceiver 3. The B-mode processor 41 generates image data for the tomographic images based on the sequentially inputted reception results, and inputs them in the volume data generator 51.

The volume data generator 51 sequentially generates the volume data Wi for each partial region Qi, based on the image d at a for the sequentially input tomographic images. Each volume data Wi is stored in the image data memory 7 by the controller 9 (refer to FIG. 9).

Furthermore, the MPR processor 52 sequentially generates image data for the MPR images of the partial regions Qi, based on the plurality of sets of volume data Wi. The cross-sectional position for this MPR image is set by, for example, a user. The cross-sectional position may be automatically set based on cross-sectional-position information E (described later).

The controller 9 causes the display part 81 to sequentially display the MPR images corresponding to the partial regions Q1 to Qk, based on the image data sequentially generated by the MPR processor 52. At this moment, the controller 9 causes the MPR images corresponding to the partial regions Q1 to Qk to be sequentially displayed in synchronization with, for example, the period T of the electrocardiogram.

Figure 10:
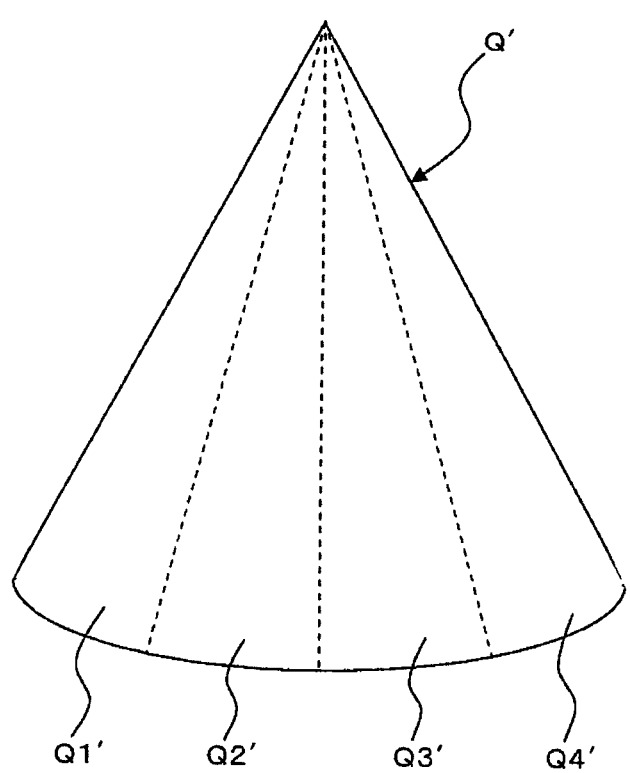
FIG. 10 is a schematic explanatory diagram for explaining an image-displaying mode in a modification example for an embodiment of an ultrasound diagnostic apparatus according to the present invention.

An example of the display mode of the MPR image in a case where the heart is divided into four partial regions Q1 to Q4 will be described with reference to FIG. 10. The display range Q of the ultrasonic image (MPR image in a specified cross-sectional position) is divided into the display ranges Q1' to Q4', which correspond to the four partial regions Q1 to Q4.

The controller 9 causes the display range Q1' to display the MPR image based on the volume data W1 corresponding to the partial region Q1. When the next one period T is passed and the image data of the MPR image based on the volume data W2 corresponding to the partial region Q2 is generated, the controller 9 causes the display range Q2' to display this MPR image. When the next one period T is passed and the image data of the MPR image based on the volume data W3 corresponding to the partial region Q3 is generated, the controller 9 causes the display range Q3' to display this MPR image. When the next one period T is passed and the image data of the MPR image based on the volume data W4 corresponding to the partial region Q4 is generated, the controller 9 causes the display range Q4' to display this MPR image.

When the period T is passed once again and the image data of the MPR image based on the volume data W1 corresponding to the partial region Q1 is generated, the controller 9 causes the display range Q1' to display a new MPR image of the partial region Q1.

Thus, the controller 9 updates, in the circulative manner, the MPR images of the partial regions Q1 to Q4, which are displayed in the display ranges Q1' to Q4', at every one period T.

Another display mode will be described hereunder. In this display mode, displayed MPR images are updated every time interval (k×period T) according to the number k of the partial regions Qi. It will be described in detail with reference to the FIG. 10. The controller 9 updates, every four periods (=4T), all of the MPR images of the partial regions Q1 to Q4, which are generated every one period T.

This display mode will be described in more detail. As described above, four new MPR images corresponding to the partial regions Q1 to Q4 are generated at every four periods. For the four new images, the controller 9 causes the MPR images of the partial region Q1, the partial region Q2, the partial region Q3 and the partial region Q4 to be displayed at one time in the display range Q1', the display range Q2', the display range Q3' and the display range Q4', respectively. That enables four display images to be updated at every four periods.

In the case of imaging with ECG-gated scan, it is possible to employ a display mode other than described above.

Based on the above preparations, a process according to the present invention will be described As illustrated in FIG. 9, the ultrasound diagnostic apparatus 10 stores the cross-sectional-position information E showing the cross-sectional position of the MPR image obtained in the past. Additionally, the ultrasound diagnostic apparatus 10 stores the volume data W having been the basis of this MPR image. The volume data W includes the number k of volume data corresponding to the partial regions Q1 to Qk of the heart.

As in the above embodiment, it is possible to store the image data of the MPR image based on the volume data W instead of storing the volume data W, or it is possible to store the image data of the MPR image based on the volume data W together with the volume data W.

In a case where a new ultrasonic image of the relevant heart is obtained using the ECG-gated scan method, the controller 9 sets a partial region of the heart intended for this-time examination, based on division information showing a division mode of the heart. The division information is stored, for example, in the information memory 6.

The division information may include, for example, information on the number k of partial regions, or information on the range for each partial region (e.g., a range for the ultrasonic scan, and a range for display of an image). The controller 9 sets the partial region for the heart, based on the division information. Additionally, the controller 9 sets a process of generating the image data by the volume data generator 51 and the MPR processor 52, based on the division information. Additionally, the controller 9 sets the number of the display ranges for displaying the MPR images, based on the division information. A description will be made below assuming the number k of the partial regions is 4.

The controller 9 transmits the cross-sectional-position information E stored in the information memory 6 to the MPR processor 52. Then, the MPR processor 52 generates image data for the MPR image in the cross-sectional position shown in the cross-sectional-position information E.

The display part 81 displays a cross-sectional image-comparing screen that is the same as in FIG. 7, for example. This cross-sectional-image-comparing screen is provided with display ranges Q' and R' (not shown), which are the same as in FIG. 10. The display range Q' displays the past MPR image. The display mode thereof is, for example, the abovementioned one-time update performed at every four period. Meanwhile, the display range R' displays the MPR image obtained by this-time examination in the same display mode (describe later).

Here, the past examination is assumed to be an examination in the resting phase for stress echocardiography, and this-time examination is assumed to be an examination in the stress phase. Accordingly, it is general that the period T' of the electrocardiogram for this-time examination is shorter than the period T for the examination in the resting phase or less stress phase (T'<T).

The controller 9 detects the period T' based on the electrocardiogram inputted from the electrocardiograph 11. The ultrasound diagnostic apparatus 10 performs processes of generating the volume data and generating the image data for the MPR image, in synchronization with the period T'. At this time, a new MPR image is generated so as to match with the cross-sectional position shown in the cross-sectional-position information E for the past examination.

The controller 9 updates, at one time, the MPR images to be displayed in the display range R' at every four periods (=4T'). At this time, the controller 9 also updates, at one time, the past MPR images in synchronization with the four periods (=4T') (in other words, one-time updates at every four periods (=4T')). Thus, both the past MPR images and the new MPR images are displayed in synchronization with the period T' (period: display update interval=1:4).

It should be noted that the display mode for the past MPR images and the new MPR images is not limited to the above. As an example thereof, in consideration with T'<T, display of the image range according to the ratio between the period T and the period T', can be omitted out of all the past MPR images. For example, in the case of T': T=1:2, the images corresponding to scan performed during the first half period T/2 are displayed in a circulative manner, in synchronization with the period T'. At this time, the range for the scan performed during each period of T and T' is the same, but the number of obtained volume data is different.

According to this modification example, it is possible to automatically obtain the tomographic image for the cross-sectional position so as to match with the tomographic image observed in the past examination, in the examination conducted for observing the time-elapsed changes in biological tissue by the ECG-gated scan method. Therefore, it is possible to easily obtain the tomographic image for the same cross-sectional position of this biological tissue.

Additionally, since the tomographic image obtained in the past examination and the tomographic image obtained in the new examination, can be displayed side-by-side, these images can be easily compared. In particular, both the tomographic images are displayed in synchronization with the period of the electrocardiograph, whereby it is possible to easily understand the condition of the heart in a desired phase of the heartbeat.

Additionally, the user can match the cross-sectional position of the new tomographic image with the cross-sectional position of the past tomographic image by simply adjusting the manner of placement of the ultrasonic probe 2 as needed. This makes it possible to easily perform an examination for observing the time-elapsed changes in biological tissue. It is also possible to shorten the examination time.

Furthermore, according to this modification example, it is possible to simultaneously display a plurality of pairs of the past tomographic image and the new tomographic image, whose cross-sectional positions are matched with each other. That enables the user to perform a comprehensive diagnosis, while comparative observation of the images of various cross-sectional positions of the biological tissues.

Modification Example 3

The ultrasound diagnostic apparatus according to this modification example functions so as to, when a imaging mode is changed, obtain the cross-section image for the cross-sectional position in accordance with the new imaging mode.

Here, an imaging mode means a type of imaging that is set beforehand according to the difference in the biological tissues intended for observation and the difference in the imaging methods. Examples of the imaging mode include a "stress echo mode" for performing a stress echocardiography examination of the heart, an "abdomen mode" for observing the inside condition of the abdomen, and a "fetus mode" for observing the condition of the fetus. The imaging mode may be called "protocol," since each mode is provided with a program (protocol) to be used.

By setting the imaging mode, the ultrasound diagnostic apparatus scans the ultrasound in the mode that is suitable for the object intended for observation and the imaging method (a program used for scanning control). Additionally, the ultrasound diagnostic apparatus performs a process of generating the image data in the mode that is suitable for the object intended for observation and so on.

In order to set the imaging mode, the user interface 8 is used. For that, the controller 9, for example, causes the display part 81 to display the screen for setting the imaging mode. The user refers to this screen and specifies a desired imaging mode using the operation part 82. The controller 9 sets each part in the apparatus to the condition according to the specified imaging mode.

An example of a process according to this embodiment will be described hereunder. In this example, the case of performing an examination in the resting phase for stress echocardiography, subsequently performing an examination for an abdomen and then back to performing an examination in the stress phase for stress echo cardiography will be described hereunder.

In stress echocardiography using, for example, the drug stress, such examination flow is employed for the case of performing another examination (in this case, the examination for an abdomen) during the period until the drug starts working.

First, the cross-sectional-position information D showing the cross-sectional position of the MPR image obtained by the examination in the resting phase is stored in the information memory 6. Additionally, volume data V1 obtained in this examination (and/or the image data for the MPR image) is stored in the image data memory 7 (refer to FIG. 1).

Once the examination for the resting phase is completed, the user changes the imaging mode into the abdomen mode by using the user interface 8. Then, the user applies the ultrasound jelly to the abdomen of the subject and placing the ultrasonic probe 2 on the abdomen, thereby performing the examination.

Once the examination for the abdomen is completed, the user puts the imaging mode back to the stress echo mode by using the user interface 8, and starts the examination for the stress phase. The controller 9 causes the display part 81 (display ranges 3001 to 3003 of the tomographic-image-comparing screen 3000) to display the MPR images obtained in the stress phase.

The controller 9 transmits the cross-sectional-position information D in the examination for the resting phase to the MPR processor 52. Thus, the MPR images of the stress phase having the cross-sectional position matched with those of the MPR images of the resting phases are generated based on the reception results obtained in the 3-dimensional ultrasonic scan by the ultrasonic probe 2, and are displayed respectively in the display ranges 3004 to 3006 of the tomographic-image-comparing screen 3000.

The user matches the cross-sectional position of the MPR image for the stress phase, which is displayed in real-time, with the cross-sectional position of the MPR image for the resting phase, by adjusting the manner of placement of the ultrasonic probe 2 as needed. Once the cross-sectional positions are matched, the user performs the specified operation, and stores volume data V2 (and/or the image data for the MPR image) for the stress phase.

According to this modification example, when the imaging mode is changed, the cross-sectional position is automatically set in accordance with the new imaging mode, so that it is possible to easily match the cross-section in an examination after the change. In particular, in the case of performing another examination during an interval period between examinations for observing the time-elapsed changes in biological tissue, it is possible to automatically obtain the tomographic image for the cross-sectional position matched with that of the tomographic image observed before another examination, and therefore, it is possible to easily obtain the tomographic images at the same cross-sectional position.

Additionally, since the tomographic image obtained before the other examination and the tomographic image obtained after the other examination are displayed side-by-side, these images can be easily comparatively observed.

Additionally, the user can match the cross-sectional position of the tomographic image after the other examination with the cross-sectional position of the tomographic image before the other examination by simply adjusting the manner of placement of the ultrasonic probe 2 as needed. This makes it possible to easily perform an examination for observing the time-elapsed changes in biological tissue. It is also possible to shorten the examination time.

Fourth Modification Example

This modification example is to perform a process based on Modification Example 3 applying the cross-sectional position according to the change of the imaging mode. In particular, a sub-mode is provided for each phase in the stress echo mode.

Once the drug stress is applied, the size of the heart may become smaller than in the resting phase. In order to deal with such phenomenon, for example, the following configuration can be made. First, it is configured so that a screen for selection of a phase is displayed on the display part 81 and a phase can be specified with the operation part 82. In particular, it is configured so that the stress phase mode can be specified at the time of shift to the stress phase. In the case of performing the examination for the stress phase in stages (e.g., low stress phase and high stress phase, etc.), it is preferable that each stress phase can be individually specified.

Figure 11A:
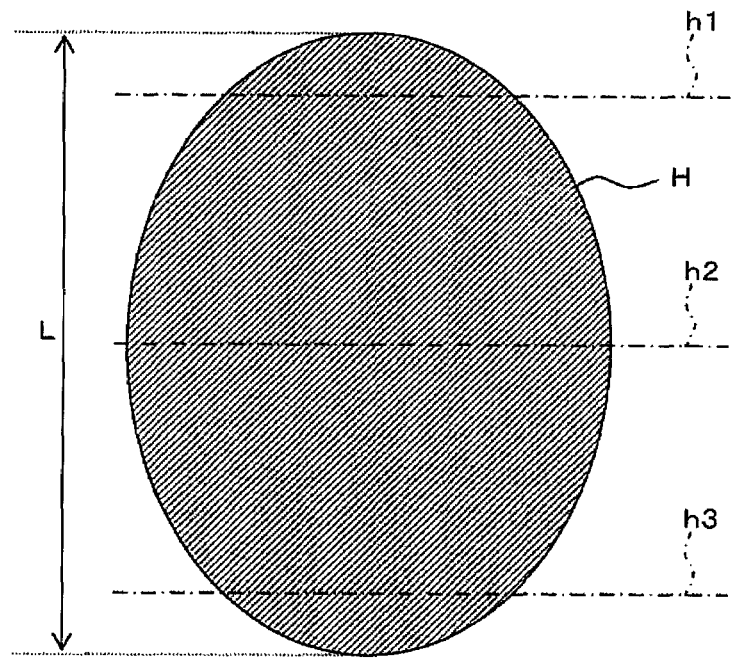
FIG. 11A and FIG. 11B are schematic explanatory diagrams for explaining a setup process of a cross-sectional position in a modification example for an embodiment of an ultrasound diagnostic apparatus according to the present invention.
Figure 11B:
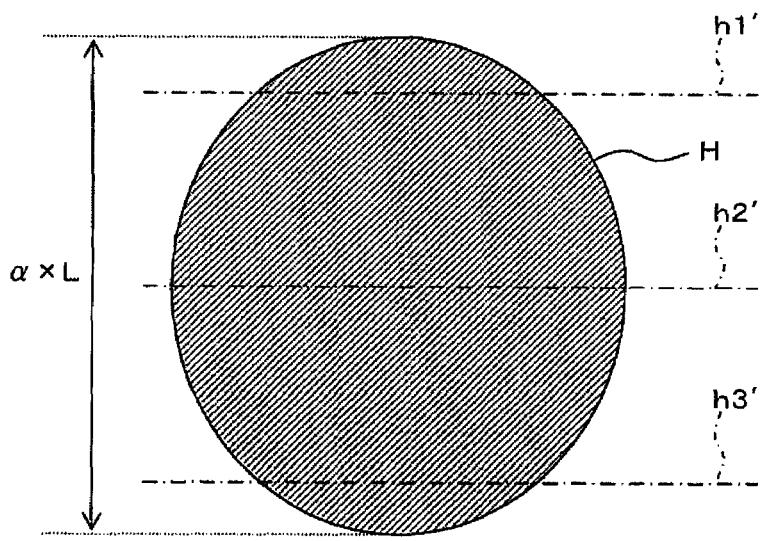

FIGS. 11A and 11B illustrate a change in size of a heart H between the resting phase and the stress phase. Here, the length from an apex to a base is considered as a size of the heart H. The length of the heart H for the resting phase is denoted by L. Additionally, the length of the heart H when the drug stress is applied is denoted by $\alpha \times L$ ($\alpha < 1$). The contraction rate $\alpha$ for the heart H is a parameter that is dependent on a phase type and a drug type.

The contraction rate $\alpha$ can be clinically obtained like an average value of the multiple clinical data. The contraction rate $\alpha$ is also obtained from the results of the examination conducted to the relevant subject in the past. The contraction rate a can be obtained by calculating $L'/L$ ($=\alpha$) in addition to measuring the length L based on the volume data V1 obtained in the resting phase, and measuring the length L' based on the volume data V2 real-time obtained in the resting phase. It is desirable to calculate the contraction rate for each stress phase, in the case of performing the examination for the stress phase in stages.

It is assumed that in the resting phase, a cross-sectional position h1 for a short-axis view of the left ventricle at an apex level, a cross-sectional position h2 for a short-axis view of the left ventricle at a papillary muscle level, and a cross-sectional position h3 for a short-axis view of the left ventricle at a base level are individually set as shown in FIG. 11A. The respective cross-sectional positions h1, h2 and h3 are represented, for example, in a three-dimensional coordinate system defined in the volume data V1. These cross-sectional positions h1, h2 and h3 are stored as the cross-sectional-position information D1 in the information memory 6.

Once the user specifies the stress phase, the controller 9 individually calculates the cross-sectional position h1' for a short-axis view of the left ventricle at the apex level, the cross-sectional position h2' for a short-axis view of the left ventricle at the papillary muscle level, and the cross-sectional position h3' for the short-axis view of the left ventricle at a base level, which are obtained in the stress phase, based on the contraction rate $\alpha$ and the cross-sectional-position information D1.

An example of the calculating process for obtaining the cross-sectional positions h1', h2' and h3' will be described hereunder. First, the controller 9 obtains the coordinates (x0, y0, z0) for the apex for the heart H and the coordinates (x4, y4, z4) for the base, based on the volume data V1 for the resting phase. Additionally, a new coordinate axis (heart length coordinate axis) $\zeta$ is set in the direction from the apex to the base, based on this xyz coordinate system. Here, the coordinate value of the apex is to be $\zeta=\zeta 0$, and the coordinate value of the base is to be $\zeta=\zeta 4$.

Additionally, it is assumed that coordinate values of intersection points between the cross-sectional positions h1, h2 and h3 for the MPR images in the resting phase and the heart length coordinate axis $\zeta$ are respectively (x1, y1, z1) ($=\zeta 1$), (x2, y2, z2) ($=\zeta 2$), and (x3, y3, z3) ($=\zeta 3$). These piece of coordinate value information are stored as the cross-sectional-position information D1 for the resting phase. Additionally, the coordinates of the apex for the heart H (x0, y0, z0) ($=\zeta 0$), and the coordinates of the base (x4, y4, z4) ($=\zeta 4$), for the resting phase are also stored as the cross-sectional-position information D1.

At the time of shift to the stress phase, the user specifies the stress phase mode using the user interface 8. Once the volume data V2 is generated in the stress phase, the controller 9 obtains the coordinates (x0', y0', z0') for the apex of the heart H and the coordinates (x4', y4', z4') for the base, based on the volume data V2. Additionally, the controller 9 obtains the coordinate value for these coordinates based on the heart length coordinate axis $\zeta$. At this time, the position of the apex is to be $\zeta=\zeta 0'$, while the position of the base is to be $\zeta=\zeta 4'$.

Additionally, the controller 9 obtains the coordinate values for the intersection points (x1', y1', z1') ($=\zeta 1'$), (x2', y2', z2') ($=\zeta 2'$), and (x3', y3', z3') ($=\zeta 3'$), between each of the cross-sectional positions h1', h2' and h3' for the stress phase and the heart length coordinate axis $\zeta$, based on the contraction rate $\alpha$ for the heart H and the coordinate values for the above intersection points in the resting phase (x1, y1, z1) ($=\zeta 1$), (x2, y2, z2) ($=\zeta 2$), and (x3, y3, z3) ($=\zeta 3$). For the contraction rate $\alpha$, the predetermined value can be used as described above, or it can be obtained at every examination based on the length L and L' of the heart H for each phase.

An example of a process of obtaining the intersection points will be described hereunder. First, distances $\Delta\zeta 1$, $\Delta\zeta 2$ and $\Delta\zeta 3$ between the apex position $\zeta=\zeta 0$ in the resting phase and each of the intersection points $\zeta=\zeta 1$, $\zeta 2$ and $\zeta 3$ are calculated. Next, the contraction rate $\alpha$ is multiplied to each of the distances $\Delta\zeta 1$, $\Delta\zeta 2$ and $\Delta\zeta 3$: $\Delta\zeta 1'=\alpha \times \Delta\zeta 1$, $\Delta\zeta 2'=\alpha \times \Delta\zeta 2$, and $\Delta\zeta 3'=\alpha \times \Delta\zeta 3$.

Subsequently, the coordinates, which are positioned the distance $\Delta\zeta 1'$, $\Delta\zeta 2'$ and $\Delta\zeta 3'$ away from the apex position $\zeta=\zeta 0'$ are individually calculated for the volume data obtained in the stress phase: $\zeta 1'=\zeta 0+\Delta\zeta 1'$, $\zeta 2'=\zeta 0+\Delta\zeta 2'$, and $\zeta 3'=\zeta 0+\Delta\zeta 3'$ (a direction from the apex to the base is to defined as a + direction for the heart length coordinate axis $\zeta$).

Each of the positions $\zeta 1'$, $\zeta 2'$ and $\zeta 3'$ is converted into a coordinate value shown in the three-dimensional coordinate system defined in the volume data. Thus, the coordinate values (x1', y1', z1'), (x2', y2', z2') and (x3', y3', z3') for the intersection points between the cross-sectional positions h1', h2' and h3' for the stress phase, and the heart length coordinate axis $\zeta$, can be obtained.

Each of the cross-sectional positions h1', h2' and h3' is set as a plane of a specified direction, such as a plane orthogonal to the heart length coordinate axis ζ. In other words, a direction of the normal line of the plane that forms the respective cross-section a positions h1', h2' and h3' is predetermined. For example, the normal direction is set to be equal to the direction of the heart length coordinate axis ζ. The controller 9 obtains a plane having the normal line and passing through the coordinate value (x1', y1', z1'), and then sets the plane to the cross-sectional position h1'. The same setting can be performed with the cross-sectional positions h2' and h3'.

The MPR processor 52 generates image data for the MPR image obtained in the cross-sectional positions h1', h2' and h3', based on the volume data obtained in the stress phase. The controller 9 causes the MPR images of the stress phase and the MPR images of the resting phase, to be displayed side-by-side.

According to this modification example, it is possible to efficiently perform an examination in the stress phase for stress echocardiography.

Another Modification Example

An example of a case of performing further examination after performing two or more examinations in the past will be described hereunder. The information memory 6 stores the cross-sectional-position information obtained in the respective past examinations. The image data memory 7 stores the volume data (and/or the image data for the MPR image) obtained in the respective past examinations. Here, each of the cross-sectional-position information and the volume data are individually associated with the examination date information showing the examination date.

In the case of performing a third-time examination and more, the controller 9 searches the cross-sectional-position information for the previous examination (latest examination performed in the past) based on the examination date information and, based on the cross-sectional-position information, sets the cross-sectional position for this-time examination. The MPR processor 52 generates image data for the MPR image in the relevant cross-sectional position, based on the volume data obtained in the previous examination.

In many cases, in the examination for observing the time-elapsed changes in biological tissue, this-time examination result and the previous examination result are comparatively observed. Therefore, according to this modification example, it is possible to increase the efficiency of such an examination.

Additionally, like the case in which there are two or more stress phases in the above embodiment, if images are obtained at three or more different dates and times, in the case of comparative observation of the images of arbitrary two dates and times, the image obtained at the earlier date, out of these two dates and times is equivalent to a "past" image, while the image obtained at the later date is equivalent to a "new" image.

Additionally, it is also possible to comparatively observe images of three or more dates and times. In that case, the image obtained at the latest date, out of these three or more dates and times is equivalent to a "new" image, while the image obtained at each date before that is equivalent to a "past" image.

It should be noted that simultaneous display of the images obtained at three or more dates and times can be applied to the case of real-time observation of images of the biological tissue, and can also be applied to the case of reviewing the images previously obtained at three or more dates and times.

Second Embodiment

A second embodiment of an ultrasound diagnostic apparatus according to the present invention will be described hereunder. In the first embodiment described above, the cross-sectional position for the MPR image generated from the volume data is pre-stored, and the relevant cross-sectional position is reproduced in a later examination. Meanwhile, in the second embodiment, a scanning position of ultrasound by an ultrasonic probe is pre-stored, and the ultrasonic scan is controlled so that the relevant scanning position is reproduced in a later examination.

[Apparatus Configuration]

Figure 12:
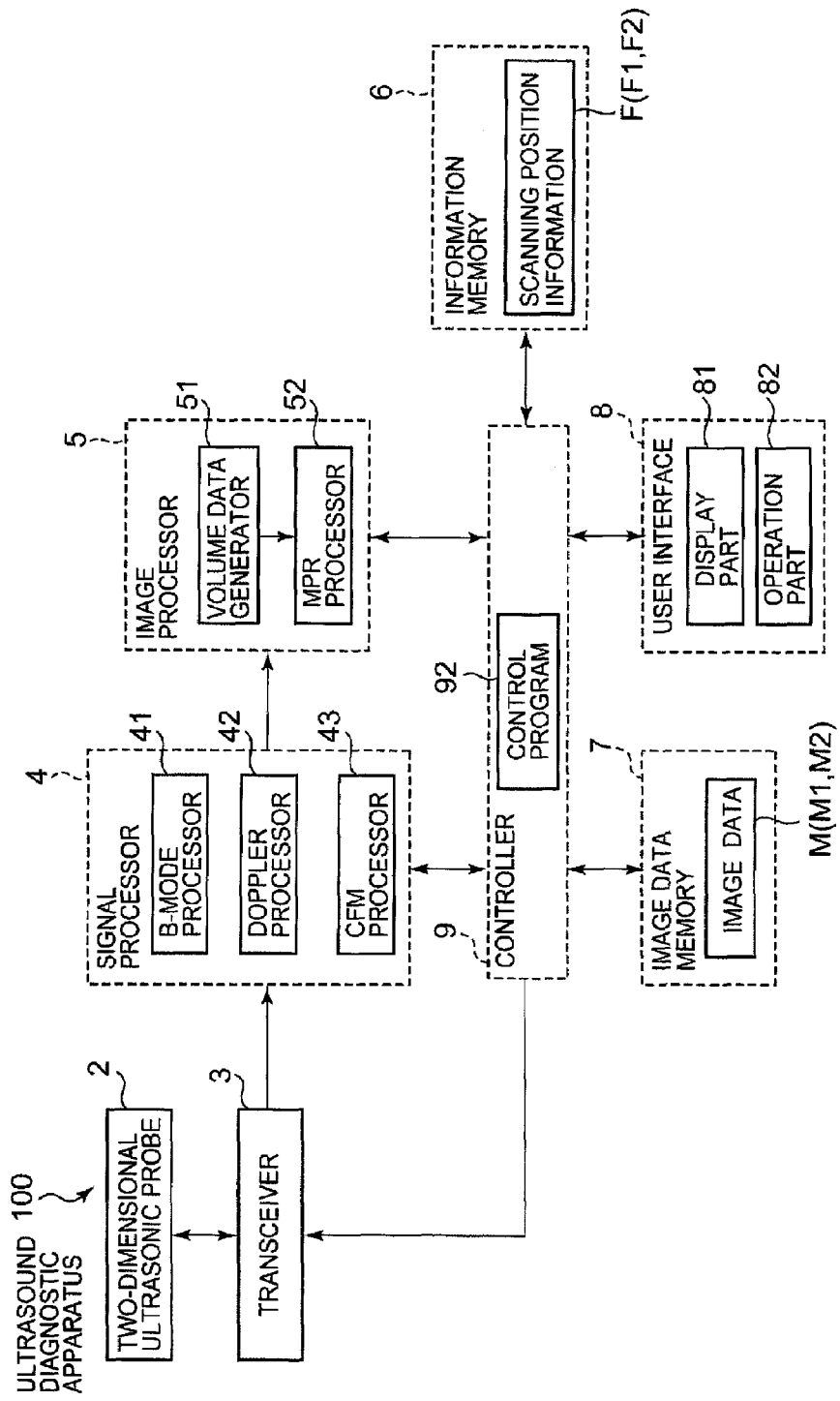
FIG. 12 is a schematic block diagram illustrating an example of the entire configuration for an embodiment of an ultrasound diagnostic apparatus according to the present invention.

FIG. 12 illustrates an example of an ultrasound diagnostic apparatus according to the second embodiment. An ultrasound diagnostic apparatus 100 has the similar configuration as the ultrasound diagnostic apparatus 1 according to the first embodiment. Below, the similar components as in the first embodiment will be denoted by the same reference numerals.

The information memory 6 stores scanning position information F that shows an ultrasonic scanning position by the ultrasonic probe 2. Additionally, the image data memory 7 stores image data M such as image data for a tomographic image and volume data.

The ultrasound diagnostic apparatus 100 is configured to perform operations that are characteristic of this embodiment, based on a control program 92.

[Usage]

Figure 13:
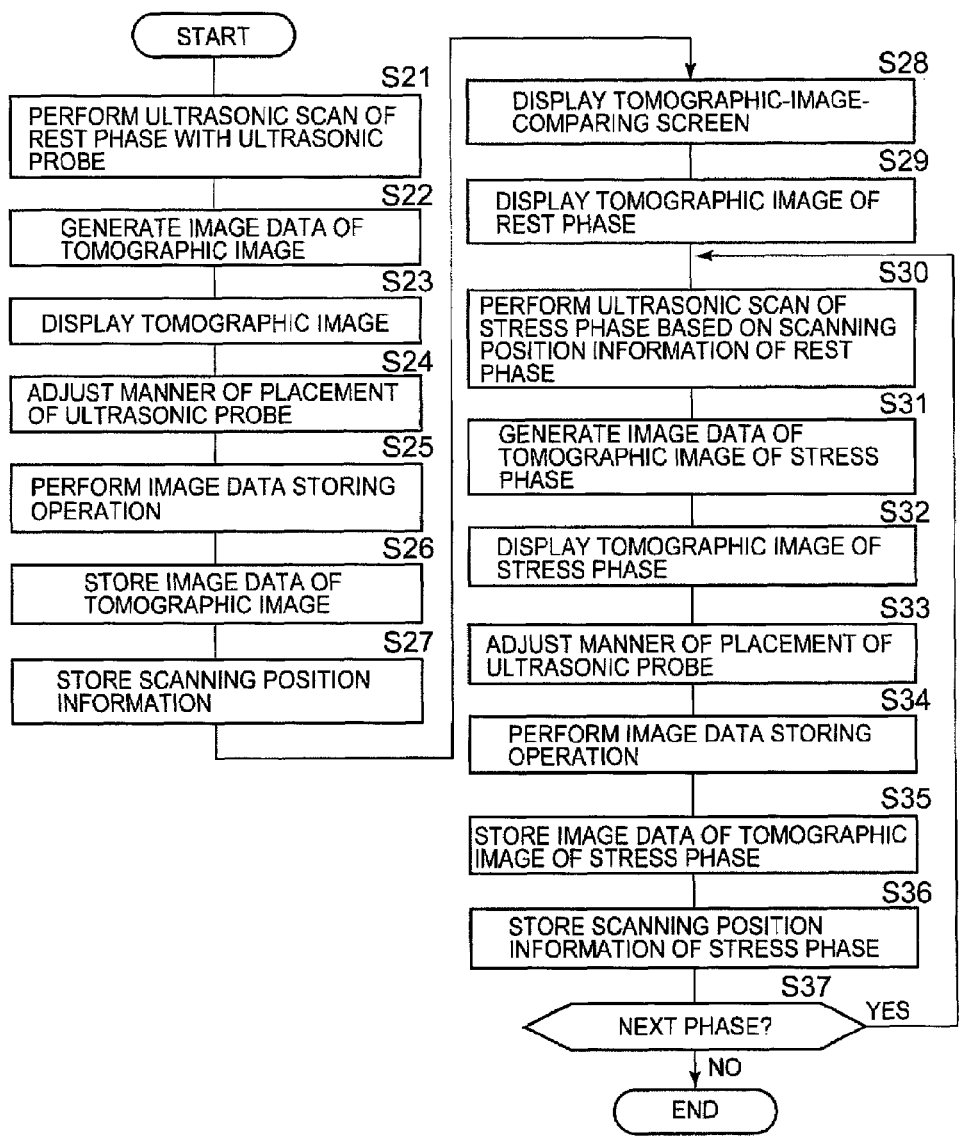
FIG. 13 is a flowchart illustrating an example of an operation mode in an embodiment of an ultrasound diagnostic apparatus according to the present invention.

The usage of the ultrasound diagnostic apparatus 100 will be described hereunder. A flow chart shown in FIG. 13 illustrates an example of a usage in the case in which the ultrasound diagnostic apparatus 100 is applied to a stress echocardiography examination.

Examination in the Resting Phase

First, an examination in the resting phase is performed. At the start, the ultrasonic scan is performed on the heart using the ultrasonic probe 2 (S21).

Here, a multi-plane scan of scanning each of a plurality of cross-sectional positions is performed. For example, a bi-plane scan of scanning each of two cross-sectional positions, a tri-plane scan of scanning each of three cross-sectional positions, or the like is performed (e.g., refer to the Japanese Unexamined Patent Application Publication No. 2004-209247). The multi-plane scan is widely used for real-time observation of biological tissue, since a series of scan can be performed in a short time, compared with a three-dimensional ultrasonic scan.

Figure 14A:
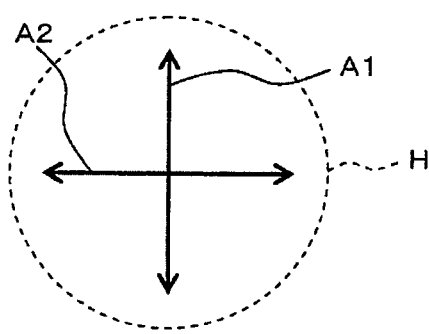
FIGS. 14A and 14B are schematic explanatory diagrams for explaining a scanning mode for a multi-plane scan of the ultrasound in an embodiment of an ultrasound diagnostic apparatus according to the present invention.
Figure 14B:
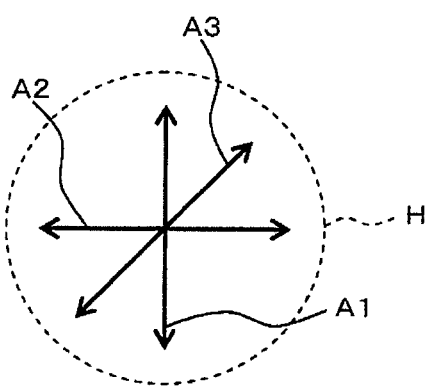

FIGS. 14A and 14B illustrates an example of the multi-plane scan. FIGS. 14A and 14B illustrates a scanning mode in the case of viewing the biological tissue (heart H) from the ultrasonic probe 2. In the bi-plane scan shown in FIG. 14A, the ultrasound is scanned along two scanning positions A1 and A2, which are orthogonal to each other. Additionally, in the tri-plane scan shown in FIG. 14B, the ultrasound is scanned along the two scanning positions A1 and A2 orthogonal to each other, and along a scanning position A3 positioned in the equiangular direction to the respective scanning positions A1 and A2. By way of example, a case of performing the bi-plane scan shown in FIG. 14A will be described below.

In the case of an apex approach, a topographic image obtained by scanning along the scanning position A1 becomes an image of an apical two-chamber view. A topographic image obtained by scanning along the scanning position A2 becomes an image of an apical four-chamber view.

These images are tomographic images whose cross sections are each a plane formed by the scanning direction of the ultrasound along each of the scanning positions A1 and A2 and the traveling direction of the ultrasound.

The reception results arising from the ultrasonic scan (bi-plane scan) in Step S21 are transmitted to the B-mode processor 41 via the transceiver 3. At this time, the reception results arising from scanning the scanning position A1 and the reception results arising from scanning the scanning position A2 are alternatively transmitted to the B-mode processor 41.

The B-mode processor 41 alternatively generates image data of the tomographic image of the apical two chamber (apical two-chamber view) and the image data of the tomographic image of the apical four chamber (apical four-chamber view), based on these reception results (S22).

The controller 9 causes the display part 81 to display the apical two-chamber view and the apical four-chamber view (S23). These images are respectively displayed, for example, in the display ranges 1004 and 1005 of the tomographic-image-comparing screen 1000 shown in FIG. 5. Additionally, the controller 9 causes each of the apical two-chamber view and the apical four-chamber view, to be displayed and updated in synchronization with a repetition interval of scanning for each of the scanning positions A1 and A2.

A user adjusts the manner of placement of the ultrasonic probe 2 on the subject as needed so that the apical two-chamber view and the apical four-chamber view are appropriately displayed (S24).

Once the apical two-chamber view and apical four-chamber view are displayed appropriately, the user performs an operation for storing the image data through the operation part 82 (S25). After receiving this operation, the controller 9 stores, in the image data memory 7, the image data (volume data) M1 for the resting phase including the image data of the apical two-chamber view (motion data) and the apical four-chamber view (motion data) (S26).

Additionally, the controller 9 stores, in the information memory 6, the scanning position information F1 showing the scanning position of the ultrasound by the ultrasonic probe 2, which is obtained when the image data M1 is obtained (S27).

The ultrasonic probe 2 comprises a plurality of ultrasonic transducers two-dimensionally arranged as described above. The transceiver 3 drives and controls the respective ultrasonic transducers based on a scanning control signal from the controller 9, thereby scanning an ultrasonic beam in a desired scanning position (in this case, the scanning positions A1 and A2).

The scanning position information F1 is generated by the controller 9 based on the scanning control signal. The scanning position information F1 includes position information showing the scanning positions A1 and A2. This position information is information showing, for example, a scanning direction and scanning angle of the ultrasound by the ultrasonic probe 2. This is the end of the examination in the resting phase.

Examination in a Stress Phase

Subsequently, the examination in the stress phase will be performed. For that, the user first causes the display part 81 to display a screen that displays the topographic images of the stress phase (S28). This screen is, for example, the tomographic-image-comparing screen 2000 shown in FIG. 6.

The controller 9 reads out the image data M1 for the resting phase, and causes the display ranges 2001 and 2002 to display the apical two-chamber view and the apical four-chamber view obtained in the resting phase, respectively (S29).

Additionally, the controller 9 reads out the scanning position information F1 for the resting phase, generates the scanning control signal for scanning the ultrasound along the scanning positions A1 and A2 shown in the scanning position information F1, and then transmits them to the transceiver 3. Once the user starts the ultrasonic scan in order to obtain the images of the stress phase, the transceiver 3 drives the respective ultrasonic transducers of the ultrasonic probe 2, based on this scanning control signal. This makes it possible to perform the ultrasonic scan along the same scanning positions A1 and A2 as in the resting phase (S30).

The reception results by the ultrasonic probe 2 are transmitted to the B-mode processor 41 through the transceiver 3. The B-mode processor 41 alternatively generates image data for the tomographic images taken along the scanning positions A1 and A2, based on this reception result (S31).

The controller 9 causes the respective display ranges 2004 and 2003 to display the tomographic image taken along the scanning position A1 and the tomographic image taken along the scanning position A2, based on these image data (S32). Each of the displayed images is a moving image that is updated at specified time intervals.

The user adjusts the manner of placement of the ultrasonic probe 2 on the subject as needed so that the cross-sectional position for the tomographic image displayed in the display range 2003 is the same as the cross-sectional position for the apical four-chamber view displayed in the display range 2001 (S33). The user may adjust the manner of placement of the ultrasonic probe 2 so that the cross-sectional position for the tomographic image displayed in the display range 2004 matches the cross-sectional position for the apical two-chamber view displayed in the display range 2002.

As described above, once one cross-sectional position is matched, another cross-sectional position is also matched. One cross-sectional position is matched, which results in that the apical four-chamber view for the stress phase in the (approximate) same cross-sectional position as the apical four-chamber view for the resting phase is displayed in the display range 2003, and the apical two-chamber view for the stress phase in the (approximate) same cross-sectional position as the apical two-chamber view for the resting phase is displayed in the display range 2004.

Once the stress phase image and the resting phase image are displayed by matching their positions, the user performs an operation for requesting storage of the image data (S34). Upon reception of this operation, the controller 9 stores, in the image data memory 7, the image data for the stress phase (volume data) M2 including the image data for the apical four-chamber view and the image data for the apical two-chamber view, which are real-time generated at the specified frame rate respectively (S35).

Additionally, the controller 9 stores, in the information memory 6, the scanning position information F2 showing the scanning position of the ultrasound obtained when the image data M2 is obtained.

If there is a next phase (S37; Y), the above steps S30 to S36 will be repeated. In this next phase, the MPR image for a phase other than the resting phase, such as the previous phase, can be displayed with the MPR image for the relevant next stress phase. After observation for all phases is completed (S37; N), the examination in the stress phase are to be ended.

[Actions and Advantageous Effects]

Actions and advantageous effects of the ultrasound diagnostic apparatus 100 are described. When obtaining the image data for the tomographic images of biological tissue such as a heart (in this case, the apical four-chamber view and the apical two-chamber view), the ultrasound diagnostic apparatus 100 stores, in the information memory 6, the scanning position information F showing the scanning position of the ultrasonic scan performed by the ultrasonic probe in order to obtain the tomographic image. Subsequently, when obtaining the image data for new tomographic image of this biological tissue, the ultrasound diagnostic apparatus 100 performs the ultrasonic scan by reproducing the scanning position shown in the scanning position information F obtained when the image data of the tomographic image has been obtained in the past, and then displays the new tomographic image obtained thereby and the past tomographic image side-by-side.

In particular, in the case of stress echocardiography, the ultrasound diagnostic apparatus 100 can display the tomographic image in real-time, while performing the ultrasonic scan for this-time phase, based on the scanning position information F for the past phase examination.

According to the ultrasound diagnostic apparatus 100, it is possible to automatically obtain the tomographic image at almost the same cross-sectional position as the tomographic image observed in the past examination, in the examination (stress echocardiography, an observation of the clinical course, and a preoperative/postoperative observation) for observing the time-elapsed changes in biological tissue. This makes it possible to easily obtain the tomographic image in the same cross-sectional position of the biological tissue. Additionally, since this embodiment is configured to perform the multi-plane scan, the real-time observation of the biological tissue can be preferably performed.

Additionally, according to the ultrasound diagnostic apparatus 100, the tomographic image obtained in the past examination and the tomographic image obtained in the new examination are displayed side-by-side, so that it possible to easily perform a comparative observation of these images.

Additionally, the user can match the cross-sectional position of the new tomographic image with the cross-sectional position of the past tomographic image by simply adjusting the manner of placement of the ultrasonic probe 2, as needed. This makes it possible to easily perform an examination such as a stress echocardiograph examination for observing the time-elapsed changes in biological tissue. It is also possible to shorten the examination time.

Furthermore, according to the ultrasound diagnostic apparatus 1, as shown in FIG. 6, it is possible to simultaneously display a plurality of pairs of the past tomographic image and the new tomographic image whose cross-sectional positions are matched with each other. That enables the user to perform a comprehensive diagnosis, during a comparative observation of the images of various cross-sectional positions of the biological tissues.

[Another Usage]

The following usage can be performed when the ultrasound diagnostic apparatus 100 shown in FIG. 12 is used. This usage is to use both an ultrasonic multi-plane scan and a three-dimensional scan with the ultrasound. The case in which this usage is applied to stress echocardiography will be herein described.

Examination in the Resting Phase

In the resting phase examination, firstly, the bi-plane scan is performed as in the aforementioned usage, and the image data M1 including the image data of the apical four-chamber view and the image data of the apical two-chamber view for the heart is obtained and stored. Additionally, the scanning position information F1 showing the scanning positions A1 and A2 of the ultrasound when these sets of image data have been stored.

Subsequently, as in the first embodiment, the volume data for the heart is generated, and the image data for the MPR image is generated. The generated MPR images (e.g., the MPR images G1, G2 and G3 for the short-axis view of the left ventricle, the MPR image G4 for the apical four-chamber view, and the MPR image G5 for the apical two-chamber view) are displayed on the tomographic image display screen 1000 (refer to FIG. 5).

The user adjusts the manner of placement of the ultrasonic probe 2 as needed to display the MPR image for the appropriate cross-sectional position. Then, the volume data V1 and the image data for the MPR image in the resting phase are stored (refer to FIG. 1). This is the end of the examination in the resting phase.

Examination in a Stress Phase

In the stress phase examination, at first, the apical four-chamber view and the apical two-chamber view in the resting phase are displayed alongside with the apical four-chamber view and the apical two-chamber view in the stress phase, as in the abovementioned usage. These tomographic images are displayed on the tomographic-image-comparing screen 2000.

At this time, the tomographic images in the stress phase are obtained by the bi-plane scan based on the scanning position information F1 for the resting phase.

The user adjusts the manner of placement of the ultrasonic probe 2 as needed so as to match the cross-sectional position of the tomographic image in the stress phase with the cross-sectional position of the tomographic image in the resting phase.

Next, the scanning mode of the ultrasound performed by the ultrasonic probe 2 is switched into a three-dimensional scan. Then, the volume data for the stress phase is generated, and the image data for the MPR image is generated. After that, the MPR image in the stress phase and the MPR image in the resting phase are displayed side by side. These MPR images are displayed on, for example, the tomographic-image-comparing screens 2000 and 3000. Alternatively, it is possible to merely store the volume data without generating and displaying the MPR images.

The user adjusts the manner of placement of the ultrasonic probe 2 as needed in order to match the cross-sectional positions of the MPR images. Then, user stores the volume data V2 and the image data for the MPR image in the stress phase. Several stress phases are repeated in accordance with the protocol types. This is the end of the examination in the stress phase.

According to this usage, it is possible to match the positions of the images in each phase by using the position of the multi-plane scan. Additionally, it is possible to perform the three-dimensional scan after the positions are matched and obtain the volume data and the MPR images. Consequently, it is possible to easily match the positions of the images. Additionally, it is possible to easily obtain the volume data and the MPR images whose positions have been matched. Furthermore, there is a merit that an examination can be performed in real time with good time resolution.

Medical Image-Processing Apparatus

A medical image-processing apparatus according to the present invention will be described hereunder. The medical image-processing apparatus comprises any computer capable of reading data generated by an ultrasound diagnostic apparatus. An example of the medical image-processing apparatus is a computer connected to the ultrasound diagnostic apparatus. Additionally, another example of the medical image-processing apparatus is a computer connected to a database such as a PACS (Picture Archiving and Communication System) that stores image data of ultrasonic images.

Figure 15:
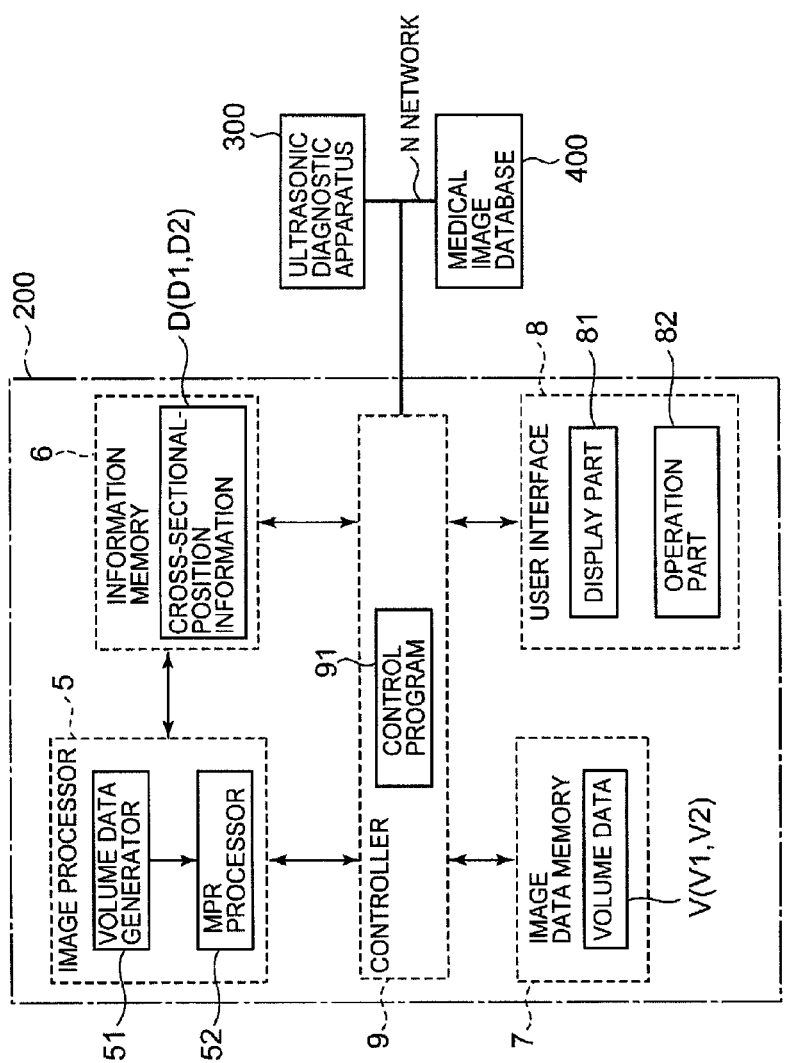
FIG. 15 is a schematic block diagram illustrating an example of the entire configuration for an embodiment of a medical image-processing apparatus according to the present invention.

FIG. 15 illustrates an example of the medical image-processing apparatus according to the present invention. In FIG. 15, components that operate similarly to those in the first embodiment are denoted by the same reference numerals.

A medical image-processing apparatus 200 comprises the image processor 5, the information memory 6, the image data memory 7, the user interface 8, and the controller 9, in the same manner as the ultrasound diagnostic apparatus 1 shown in FIG. 1.

The image processor 5 functions as an example of an "image data generator" in the present invention. The information memory 6 functions as an example of a "memory" in the present invention. The display part 81 functions as an example of a "display part" in the present invention. Additionally, the controller 9 functions as an example of a "controller" in the present invention.

This medical image-processing apparatus 200 is connected to an ultrasound diagnostic apparatus 300 and a medical image database 400 via a network N such as a LAN (local area network). For data communication via the network N, protocol communication such as a DICOM is used. The controller 9 comprises a network card for performing data communication via the network N. The ultrasound diagnostic apparatus 300 has an ultrasonic probe capable of performing three-dimensional scan.

An example of an operation performed by the medical image-processing apparatus 200 will be described hereunder. The image data for the ultrasonic image is inputted from the ultrasound diagnostic apparatus 300 or the medical image database 400 to the medical image-processing apparatus 200.

In the case in which the image data for the B-mode images (tomographic images) are inputted, the volume data generator 51 generates the volume data based on these image data. The MPR processor 52 generates image data for the MPR image, based on this volume data, as in the first embodiment.

On the other hand, in the case in which the inputted image data is volume data, the MPR processor 52 generates image data for the MPR image based on this volume data. The volume data and the image data for the MPR image are stored in the image data memory 7 by the controller 9.

An example of a usage of the medical image-processing apparatus 200 will be described hereunder. First, data for a comparative observation is obtained from the ultrasound diagnostic apparatus 300 or the medical image database 400. This data includes the image data for the ultrasonic images obtained at a plurality of examination dates.

In the case in which the image data is obtained from the ultrasonic image apparatus 300, the image data obtained by the ultrasound diagnostic apparatus 300 is inputted to the medical image-processing apparatus 200 at the specified timing.

Alternatively, in the case in which it is obtained from the medical image database 400, for example, the controller 9 causes the display part 81 to display a patient list. The user selects and specifies a desired patient from this list. The controller 9 transmits, to the medical image database 400, the patient identification information such as a patient ID of the specified patient. The medical image database 400 searches the image data for the ultrasonic image of the relevant patient, using this patient identification information as a search key, and transmits them to the medical image-processing apparatus 200. It is also possible to configure so as to specify the examination date, search the image data for the specified examination date, and input it to the medical image-processing apparatus 200.

In the case in which the image data that has been externally input is the image data for the B-mode image, the medical image-processing apparatus 200 generates the volume data based on that, and stores it in the memory 7. Alternatively, in the case in which the image data that has been externally input is the volume data, that is directly stored in the data memory 7.

As described above, the volume data V1 and V2 are stored in the image data memory 7 as shown in FIG. 15. Here, the volume data V1 corresponds to the first examination date in an observation of the clinical course, while the volume data V2 corresponds to the second examination date.

At first, the user causes the display part 81 to display the MPR image based on the volume data V1. At this time, the user set the cross-sectional position by performing the specified operation. In the case in which the cross-sectional position that has been set is a short-axis view of the left ventricle, the controller 9 causes display ranges 3001 to 3003 of a tomographic-image-comparing screen 3000, to respectively display MPR images G1 to G3 of the short-axis view of the left ventricle.

In the case in which the cross-sectional position having been set is an apical four-chamber view and an apical two-chamber view, the MPR images G4 and G5 corresponding thereto are displayed in a tomographic-image-comparing screen 2000.

The controller 9 generates the cross-sectional-position information D1 showing the set cross-sectional position, and stores them in the information memory 6.

Here, in the case in which observation of the image obtained on the first examination date was performed in the past, and a comparative observation between the images obtained on the first and the second examination date is performed for this time, it is possible, at the past time-point for setting the cross-sectional position of the MPR image, to generate the cross-sectional-position information D1 showing this cross-sectional position, and store them in the information memory 6.

The MPR processor 52 generates image data for the MPR image in the relevant cross-sectional position, based on the cross-sectional position shown in the cross-sectional-position information D1, and the volume data V2. This MPR image means an MPR image for the relevant cross-sectional position obtained on the second examination date.

The controller 9 causes the display part 81 to display the MPR image obtained on the second examination date together with the MPR image obtained on the first examination date. Thus, for example, the display ranges 3001 to 3003 of the tomographic-image-comparing screen 3000 respectively displays a short-axis view of the left ventricle G1 to G3 obtained on the first examination date, and the display ranges 3004 to 3006 of the tomographic-image-comparing screen 3000 respectively displays a short-axis view of the left ventricle G1' to G3' obtained on the second examination date.

The user can accordingly changes the cross-sectional positions of the short-axis view of the left ventricles G1' to G3' as needed, in order to match them with the cross-sectional positions of the short-axis view of the left ventricles G1 to G3. On the contrary, the user can accordingly changes the cross-sectional positions of the short-axis view of the left ventricle views G1 to G3, in order to match them with the cross-sectional positions of the short-axis view of the left ventricle views G1' to G3'.

This medical image-processing apparatus 200 is capable of automatically matching the cross-sectional positions of the tomographic images when displaying the tomographic images that have been respectively obtained at different dates, in the case of the examination for observing the time-elapsed changes in biological tissue. This makes it possible to easily obtain the tomographic image in the same cross-sectional position of the biological tissue.

The ultrasound diagnostic apparatus 200 is capable of displaying the tomographic images obtained on the different examination side-by-side in the condition in which the cross-sectional positions thereof are matched, which makes it possible to easily comparatively observe these images.

Additionally, the user can match the cross-sectional positions of the tomographic images obtained on different dates by simply adjusting the manner of placement of the ultrasonic probe 2. This makes it possible to easily perform an examination such as a stress echocardiography for observing the time-elapsed changes in biological tissue. It is also possible to shorten the examination time.

The medical image-processing apparatus 200 is capable of applying any modification examples described in the first embodiment as needed.

Program

A program according to the present invention will be described hereunder. The programs 91 and 92 described in the first embodiment and second embodiment, as well as the control program 91 for the medical image-processing apparatus 200, correspond to an example of a program according to the present invention.

The control programs 91 and 92 cause a computer to execute the processes described in the embodiments above and the modification examples thereof. The control programs 91 and 92 are stored beforehand in a storage unit such as a hard disk drive incorporated into the computer. Additionally, it is also possible to make a configuration so that the control programs 91 and 92 are stored beforehand on a server or the like on a network such as a LAN and then the computer reads this out for execution.

The control programs 91 and 92 can be stored on an arbitrary computer-readable storage media. Examples of this storage media include, an optical disk, a magneto-optical disk (e.g., CD-ROM, DVD-RAM, DVD-ROM, MO), a magnetic storage medium (e.g., hard disk, Floppy® disk, ZIP drive), and a semiconductor memory.

Another Modification Example

In the embodiments described above, stress echocardiography examination performed by an apex approach has been described, but examinations using the present invention can be applied to an arbitrary approach, such as a parasternal approach, an approach via the liver, and an approach from the neck.

Here, "approach" refers to the manner of placement of an ultrasonic probe for obtaining an image of biological tissue, or in other words, a transmission direction (reception direction) of ultrasound to the biological tissue. By taking different approaches, images in which the biological tissue from different directions is viewed can be obtained.

Two or more approaches may be combined for the actual examination. The preferred configuration for the case of performing the examination (stress echocardiography) in a combination of the apex approach and the parasternal approach will be described with reference to FIG. 16.

Figure 16:
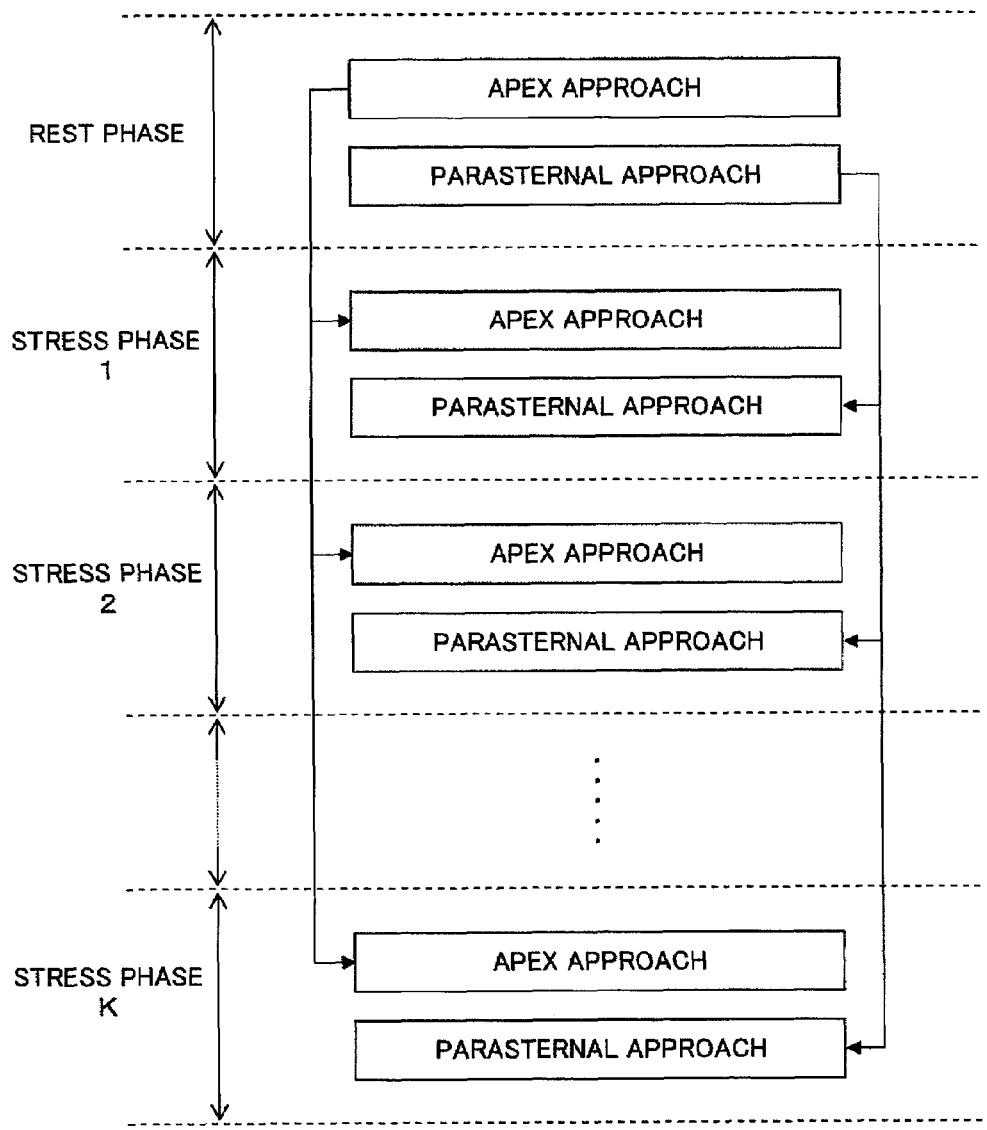
FIG. 16 is a schematic explanatory diagram for explaining a modification example for an embodiment of an ultrasound diagnostic apparatus and a medical image-processing apparatus according to the present invention.

In stress echocardiography shown in FIG. 16, each of the resting phase, stress phase 1, stress phase 2 . . . , and stress phase K (K is an integer that is equal to or more than 1) is configured to be performed with examination via the apex approach and an examination via the parasternal approach.

The control program 91 (or the control program 92) described in the embodiments above preliminarily includes protocol for the apex approach and protocol for the parasternal approach. The case of using the ultrasound diagnostic apparatus 1 (refer to FIG. 1) in the first embodiment will be described hereunder. It should be noted that the same could be configured with the abovementioned medical image-processing apparatus 200.

In the resting phase, a user specifies an apex approach by operating the operation part 82. The controller 9 selects protocol used for the apex approach in the control program 91 and causes the ultrasound diagnostic apparatus 1 to execute the following process.

The user places an ultrasonic probe 2 on the body surface adjacent to an apex of the heart for performing a three-dimensional scan via ultrasound. That enables the MPR image to be displayed on the display part 81. The user observes this MPR image. The controller 9 mutually associates the image data (volume data, etc. for imaging performed by the apex approach in the resting phase, the cross-sectional-position information showing the cross-sectional position of the observed image, and the identification information for the approach (e.g., identification information in the protocol) and then stores them. Here, the image data is stored in the image data memory 7, and the cross-sectional-position information and identification information for the approach are stored in the information memory 6. The identification information for the approach should be set beforehand.

Next, the user specifies a parasternal approach by operating the operation part 82. The controller 9 selects protocol used for the parasternal approach in the control program 91, and causes the ultrasound diagnostic apparatus 1 to execute the following process.

The user places the ultrasonic probe 2 on the body surface adjacent to a parasternal part for performing a three-dimensional scan via ultrasound and then observes the image (MPR image) displayed on the display part 81. The controller 9 mutually associates the image data (volume data, etc.) for imaging performed by the parasternal approach for the resting phase, the cross-sectional-position information showing the cross-sectional position of the observed image, and the identification information for the approach and then stores these in the information memory 6 and in the image data memory 7.

Subsequently, in the stress phase 1, a user specifies the apex approach by operating the operation part 82. The user places the ultrasonic probe 2 on the body surface adjacent to an apex part for performing a three-dimensional scan via ultrasound and then observes the image (MPR image) displayed on the display part 81.

Here, the controller 9 obtains, from the information memory 6, the cross-sectional-position information associated with the identification information for the specified approach (apex approach). The MPR processor 52 generates image data for the MPR image obtained by the apex approach in the stress phase 1, based on the cross-sectional position shown this cross-sectional-position information, and the volume data generated by the volume data generator 51.

The controller 9 causes the display part 81 to display the MPR image based on this image data together with the MPR image obtained by the apex approach in the resting phase. The user adjusts the manner of placement of the ultrasonic probe 2 so that the cross-sectional position of the MPR image for the stress phase 1 matches the cross-sectional position of the MPR image for the resting phase.

This makes it possible to compare the conditions in the (approximate) same cross-sectional positions in the resting phase and in the stress phase 1. The volume data, the cross-sectional-position information, and the identification information for the protocol for the apex approach in the stress phase 1 are mutually associated and then stored in the information memory 6 and in the image data memory 7.

Next, the user specifies the parasternal approach by operating the operation part 82. The user places the ultrasonic probe 2 on the body surface adjacent to the parasternal part for performing a three-dimensional scan via ultrasound and then observes the image (MPR image) displayed on the display part 81.

Here, the controller 9 obtains, from the image data memory 7, the cross-sectional-position information associated with the identification information for the specified approach (parasternal approach). The MPR processor 52 generates image data for the MPR image obtained by the parasternal approach in the stress phase 1, based on the cross-sectional position shown in this cross-sectional-position information, and the volume data generated by the volume data generator 51.

The controller 9 causes the display part 81 to display the MPR image based on this image data together with the MPR image obtained by the parasternal approach in the resting phase. The user adjusts the manner of placement of the ultrasonic probe 2 so that the cross-sectional position of the MPR image for the stress phase 1 matches the cross-sectional position of the MPR image for the resting phase.

This makes it possible to compare the conditions in the (approximate) same cross-sectional positions in the resting phase and in the stress phase 1. The volume data, the cross-sectional-position information, and the identification information for the protocol obtained in the parasternal approach for the stress phase 1 are mutually associated and then stored in the information memory 6 and in the image data memory 7.

With respect to each stress phase 2 to K, the same process as the stress phase 1 will be performed. In other words, in the case of the apex approach for each stress phase 2 to K, the MPR image obtained by the apex approach for the resting phase (or the stress phase before the relevant stress phase) as well as the MPR image for the relevant stress phase in the (approximate) same cross-sectional position as this MPR image are displayed. The volume data, the cross-sectional-position information, and the identification information for the protocol obtained in the apex approach for the relevant stress phase are mutually associated and then stored in the information memory 6 and in the image data memory 7.

Meanwhile, in the case of the parasternal approach for each stress phase 2 to K, the MPR image obtained by the parasternal approach for the resting phase (or the stress phase before the relevant stress phase) as well as the MPR image for the relevant stress phase in the (approximate) same cross-sectional position as this MPR image are displayed. The volume data, the cross-sectional-position information, the identification information for the protocol obtained in the parasternal approach for the relevant stress phase are mutually associated and then stored in the information memory 6 and in the image data memory 7.

By using the configuration as described above, even if two or more types of approaches are taken in each phase (or each examination date), it is possible to easily obtain the tomographic images in the same cross-sectional positions with respect to each approach. It is also possible to improve the simplification and time shortening of the examination.

The configuration for the relevant modification example can be applied to the above-mentioned second embodiment of the ultrasound diagnostic apparatus 100 (refer to FIG. 12). More specifically, first, the scanning position information of the ultrasonic probe 2 for biological tissue such as a heart is stored with respect to each of two or more approaches. Then, with respect to each of the two or more approaches, the ultrasonic probe 2 is controlled so that the ultrasound is transmitted to the scanning position shown in the scanning position information stored when the relevant approach was taken in the past. Additionally, image data for the new tomographic image is generated, based on the reception result of the ultrasound transmitted to this scanning position and then the past tomographic image and the new tomographic image in the relevant approach are displayed side-by-side.

According to this configuration, even if two or more types of approaches are taken in each phase (date), it will be possible to easily obtain tomographic images for the same cross-section of the biological tissue for each approach. It is a so possible to improve simplification and time shortening of the examination.

The case of taking two approaches in each phase has been described herein, but even in the case of taking three or more approaches in each phase, the same process can be performed for each approach.

Additionally, it is not necessary for all approaches for each phase to be taken, and only some of the approaches may be selectively taken. For example, the user may select the approach.

Furthermore, the present invention can be accordingly applied to examinations for biological tissues other than a heart.

What is claimed is:

1. An ultrasound diagnostic apparatus comprising:
   an ultrasonic probe configured to transmit ultrasound while three-dimensionally scanning, and receive ultrasound reflected by a biological tissue;
   an image data processor configured to generate image data of a tomographic image of biological tissue based on reception results of ultrasound and to generate image data of an MPR (Multi-Planar Reconstruction) image based on the volume data;
   a memory configured to store cross-sectional-position information showing a cross-sectional position of the tomographic image with regard to a first image data of a first MPR image generated by the image data processor taken at a first time;
   a display; and
   a controller configured to control the image data processor so as to, when a second image data representing a tomographic image of the biological tissue is generated by the image data processor based on reception results of new ultrasound taken at a second time, cause the display to display the second image data of a second MPR image having a cross sectional position identical to a cross sectional position of the first image data of the first MPR image.

2. The ultrasound diagnostic apparatus according to claim 1, further comprising a user interface, wherein:
   the image data processor is configured to generate the first image data and the second image data, each of which is an MPR image of the cross-sectional position designated by the user interface; and the controller is configured to cause the display to display the first image data and the second image data side by side.

3. The ultrasound diagnostic apparatus according to claim 1, further comprising a user interface configured to change an imaging mode that includes a scanning pattern of ultrasound by the ultrasonic probe and a generating pattern of image data of an MPR image by the image data processor, wherein:

the memory is configured to store the cross-sectional-position information so as to be associated with an imaging mode used when image data of an MPR image has been generated; and when an imaging mode is changed by the user interface, the controller is configured to use a cross-sectional position shown in cross-sectional-position information associated with the imaging mode after the change, of cross-sectional-position information stored in the memory.

4. The ultrasound diagnostic apparatus according to claim 1, wherein:

the first image data and the second image data comprise image data of each of MPR images of two or more cross-sectional positions different from each other;

the memory is configured to store cross-sectional-position information including a cross-sectional position of each of the two or more MPR images included in the first image data; and the controller is configured to cause the display to display side by side, two or more MPR images included respectively in the first and second image data.

5. The ultrasound diagnostic apparatus according to claim 1, wherein the controller causes the display to display a past tomographic image and a new tomographic image side by side.

6. The ultrasound diagnostic apparatus according to claim 1, wherein the cross-sectional-position information indicates a position of a tomographic image on a scanning region of three-dimensional scanning by the ultrasonic probe.

* * * * *